United States Patent [19]

Edwards et al.

[11] Patent Number: 5,599,346
[45] Date of Patent: Feb. 4, 1997

[54] RF TREATMENT SYSTEM

[75] Inventors: Stuart D. Edwards, Los Altos; James Baker; Bruno Strul, both of Palo Alto; Ronald G. Lax, Grass Valley, all of Calif.

[73] Assignee: ZoMed International, Inc., Mountain View, Calif.

[21] Appl. No.: 295,200

[22] Filed: Aug. 24, 1994

Related U.S. Application Data

[63] Continuation-in-part of Ser. No. 148,439, Nov. 8, 1993, Pat. No. 5,458,597.

[51] Int. Cl.⁶ .................................................. A61B 17/39
[52] U.S. Cl. .......................... 606/41; 606/48; 606/38; 606/39; 607/101
[58] Field of Search ................. 606/32–34, 37–42, 606/45–50; 128/642; 604/22; 607/101, 102

[56] References Cited

U.S. PATENT DOCUMENTS

| | | |
|---|---|---|
| 3,987,795 | 10/1976 | Morrison et al. |
| 3,991,770 | 11/1976 | LeVeen . |
| 4,033,351 | 7/1977 | Hetzel . |
| 4,043,342 | 8/1977 | Morrison, Jr. . |
| 4,121,592 | 10/1980 | Whalley . |
| 4,237,898 | 12/1980 | Whalley . |
| 4,289,135 | 9/1981 | Nordenström et al. . |
| 4,303,636 | 12/1981 | Gordon . |
| 4,346,715 | 8/1982 | Gammell . |
| 4,411,266 | 10/1983 | Cosman . |
| 4,565,200 | 1/1986 | Cosman . |
| 4,574,782 | 3/1986 | Borrelli et al. . |
| 4,586,490 | 5/1986 | Katz . |
| 4,660,571 | 4/1987 | Hess et al. . |
| 4,763,671 | 8/1988 | Goffinet . |
| 4,800,899 | 1/1989 | Elliott . |
| 4,838,265 | 7/1989 | Cosman et al. . |
| 4,907,589 | 3/1990 | Cosman . |
| 4,920,978 | 5/1990 | Colvin . |
| 4,931,047 | 6/1990 | Broadwin et al. . |
| 4,940,064 | 7/1990 | Desai . |
| 4,945,912 | 8/1990 | Langberg . |
| 4,976,680 | 12/1990 | Hayman et al. . |
| 4,976,711 | 12/1990 | Parins et al. . |
| 5,003,991 | 4/1991 | Takayama et al. . |
| 5,009,656 | 4/1991 | Reimels . |
| 5,013,312 | 5/1991 | Parins et al. . |
| 5,015,227 | 5/1991 | Broadwin et al. . |
| 5,026,959 | 6/1991 | Ito et al. . |
| 5,047,027 | 9/1991 | Rydell . |

(List continued on next page.)

Primary Examiner—Angela D. Sykes
Assistant Examiner—Michael Peffley
Attorney, Agent, or Firm—Wilson Sonsini Goodrich & Rosati

[57] ABSTRACT

An RF treatment system includes first and second catheters with first and second needle electrodes positioned at least partially in lumens of the first and second catheters. Each electrode is surround by a insulator sleeve which is slideable along the electrode and defines an ablation surface. An RF power source is coupled to the first and second needle electrodes. The electrodes provide bipolar RF ablation between the two, defining an ablation volume. A deflectable introducer has a laterally deflectable distal end and an ablation volume temperature sensor positioned at the distal end. The deflectable introducer is advanced in and out of the electrodes distal ends to measure a temperature of tissue in the ablation volume. The treatment system can include more than two electrodes, such as two pairs of electrodes. Further, the system can include a needle electrode extension with a laterally deflectable distal end. The needle electrode extension is positioned in at least one of the distal ends of one of the needle electrodes. It is advanced in and out of the needle electrode distal end to provide monopolar ablation. Additionally, the RF treatment system provides for the introduction of an infusion media, including but not limited to a chemotherapeutic agent, through distribution ports in the needle electrodes, or through one or more infusion devices that can house the needle electrodes and their respective catheters.

27 Claims, 21 Drawing Sheets

U.S. PATENT DOCUMENTS

| | | |
|---|---|---|
| 5,057,107 | 10/1991 | Parins et al. . |
| 5,059,199 | 10/1991 | Okada et al. . |
| 5,067,952 | 11/1991 | Gudov et al. . |
| 5,071,419 | 12/1991 | Rydell et al. . |
| 5,078,717 | 1/1992 | Parins et al. . |
| 5,080,660 | 1/1992 | Buelna . |
| 5,084,045 | 1/1992 | Helenowski . |
| 5,085,659 | 2/1992 | Rydell . |
| 5,100,423 | 3/1992 | Fearnot . |
| 5,115,818 | 5/1992 | Hollerman et al. . |
| 5,125,928 | 6/1992 | Parins et al. . |
| 5,128,147 | 7/1992 | LeVeen et al. . |
| 5,183,455 | 2/1993 | Hayman et al. . |
| 5,190,539 | 3/1993 | Fletcher et al. . |
| 5,197,466 | 3/1993 | Marchowsky et al. . |
| 5,197,963 | 3/1993 | Parins . |
| 5,205,289 | 4/1993 | Hardy et al. . |
| 5,207,675 | 5/1993 | Canady . |
| 5,215,103 | 6/1993 | Desai . |
| 5,217,458 | 6/1993 | Parins . |
| 5,246,438 | 9/1993 | Langberg . |
| 5,251,645 | 8/1993 | Fenn . |
| 5,252,922 | 8/1993 | Larson, III . |
| 5,267,994 | 12/1993 | Gentelia et al. . |
| 5,277,696 | 1/1994 | Hagen . |
| 5,281,213 | 1/1994 | Milder et al. . |
| 5,290,286 | 3/1994 | Parins . |
| 5,300,068 | 4/1994 | Rosar et al. . |
| 5,304,214 | 4/1994 | Deford et al. . |
| 5,336,222 | 8/1994 | Durgin, Jr. et al. ............... 606/50 |
| 5,365,926 | 11/1994 | Desai . |
| 5,385,544 | 1/1995 | Edwards et al. ................. 604/22 |
| 5,397,339 | 3/1995 | Desai . |
| 5,403,311 | 4/1995 | Abele et al. ..................... 606/50 |
| 5,411,025 | 5/1995 | Webster, Jr. . |

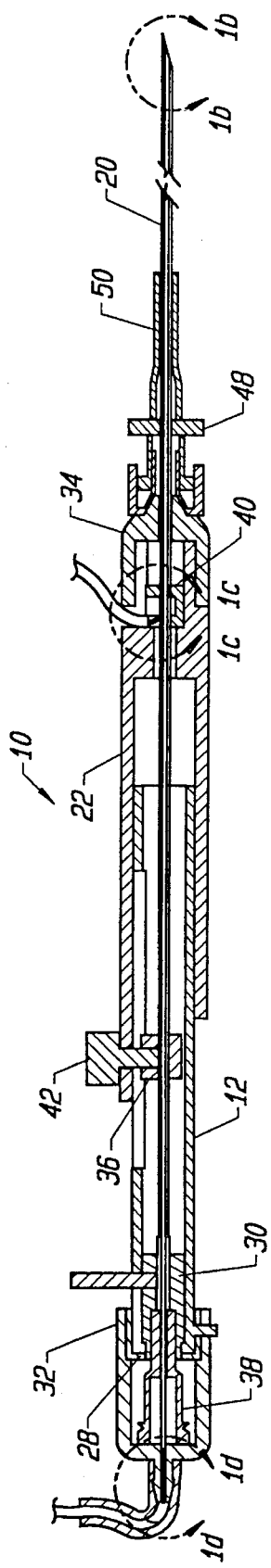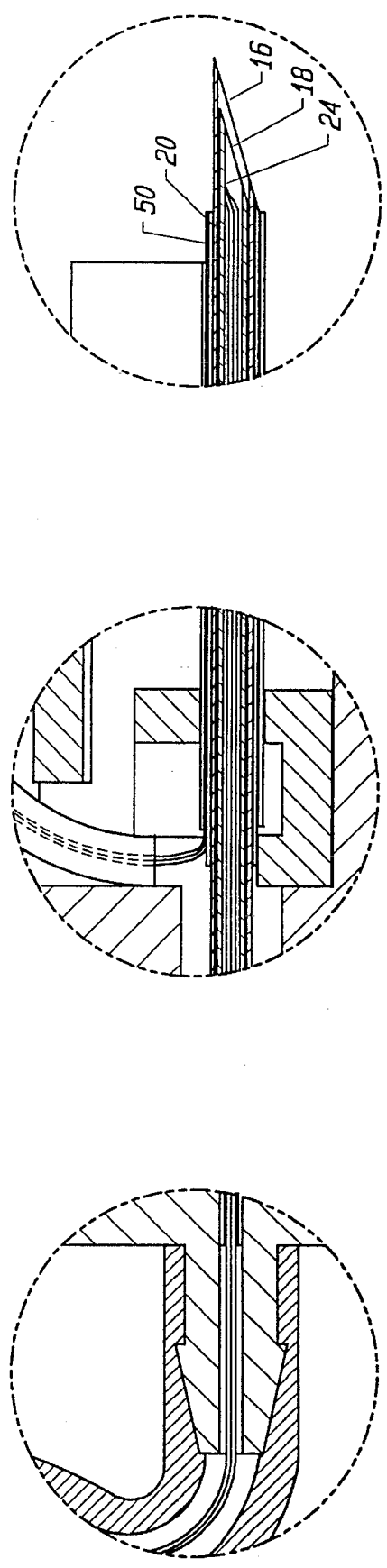
FIG. 1a
FIG. 1b
FIG. 1c
FIG. 1d

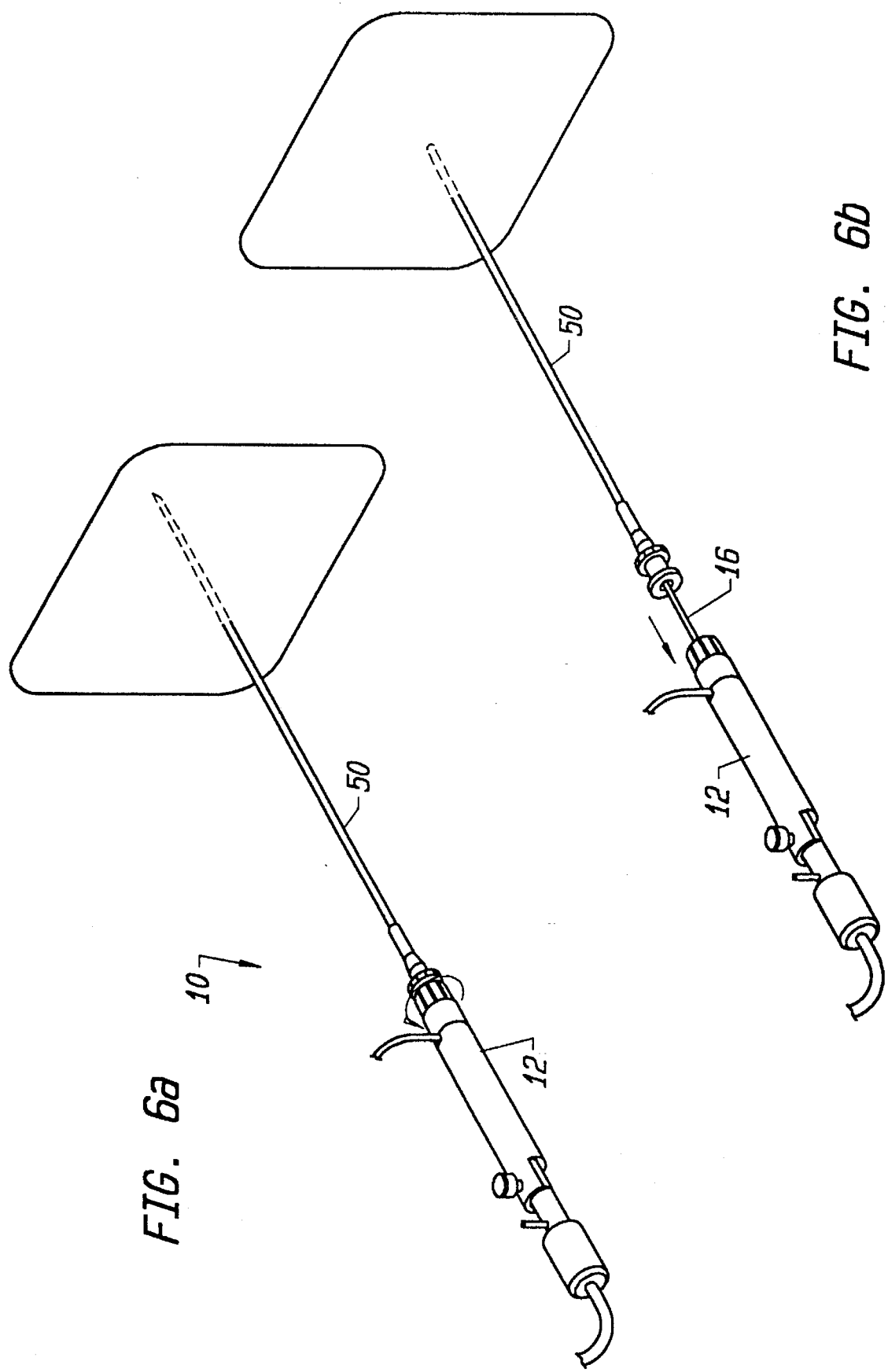

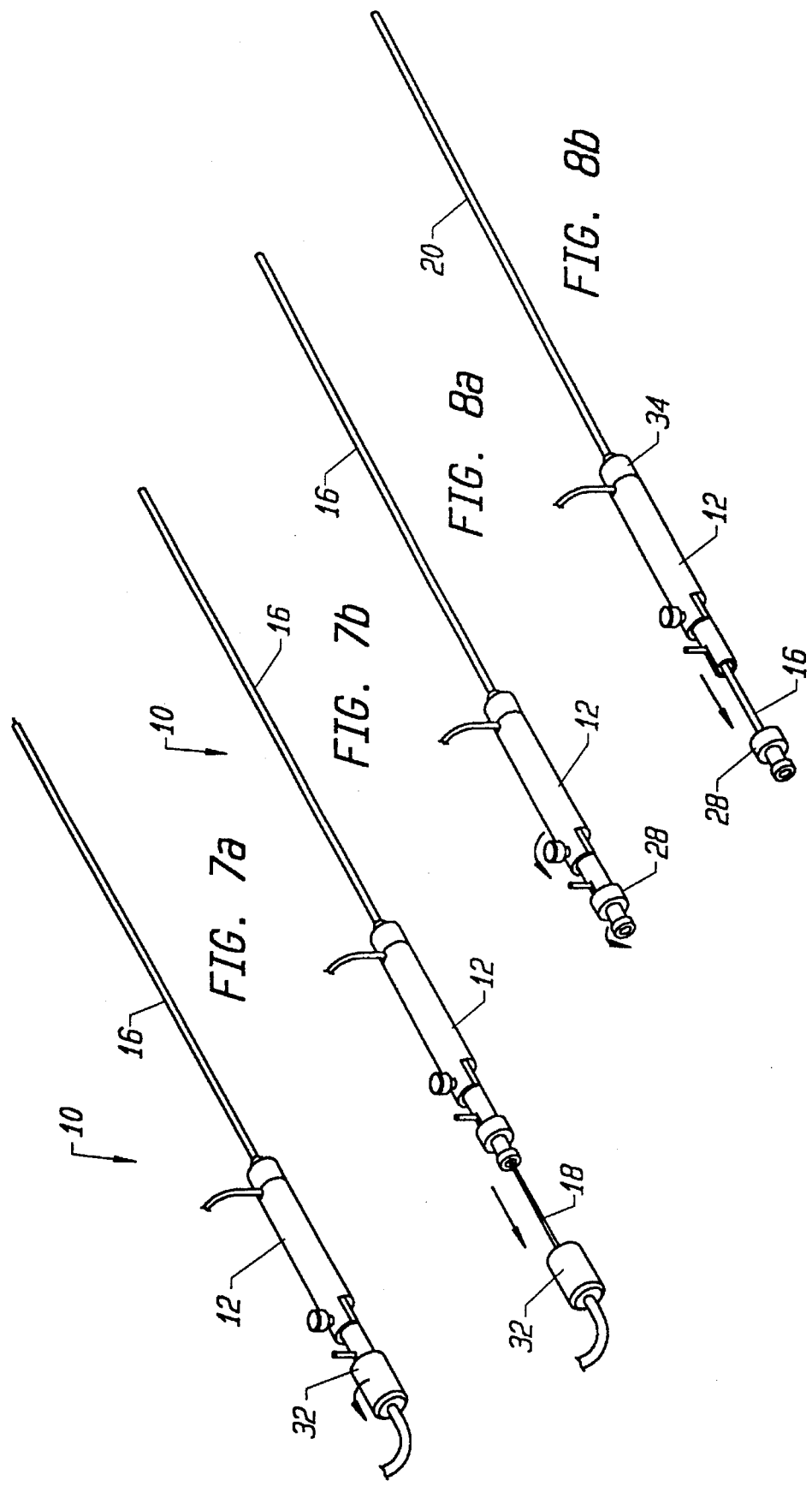

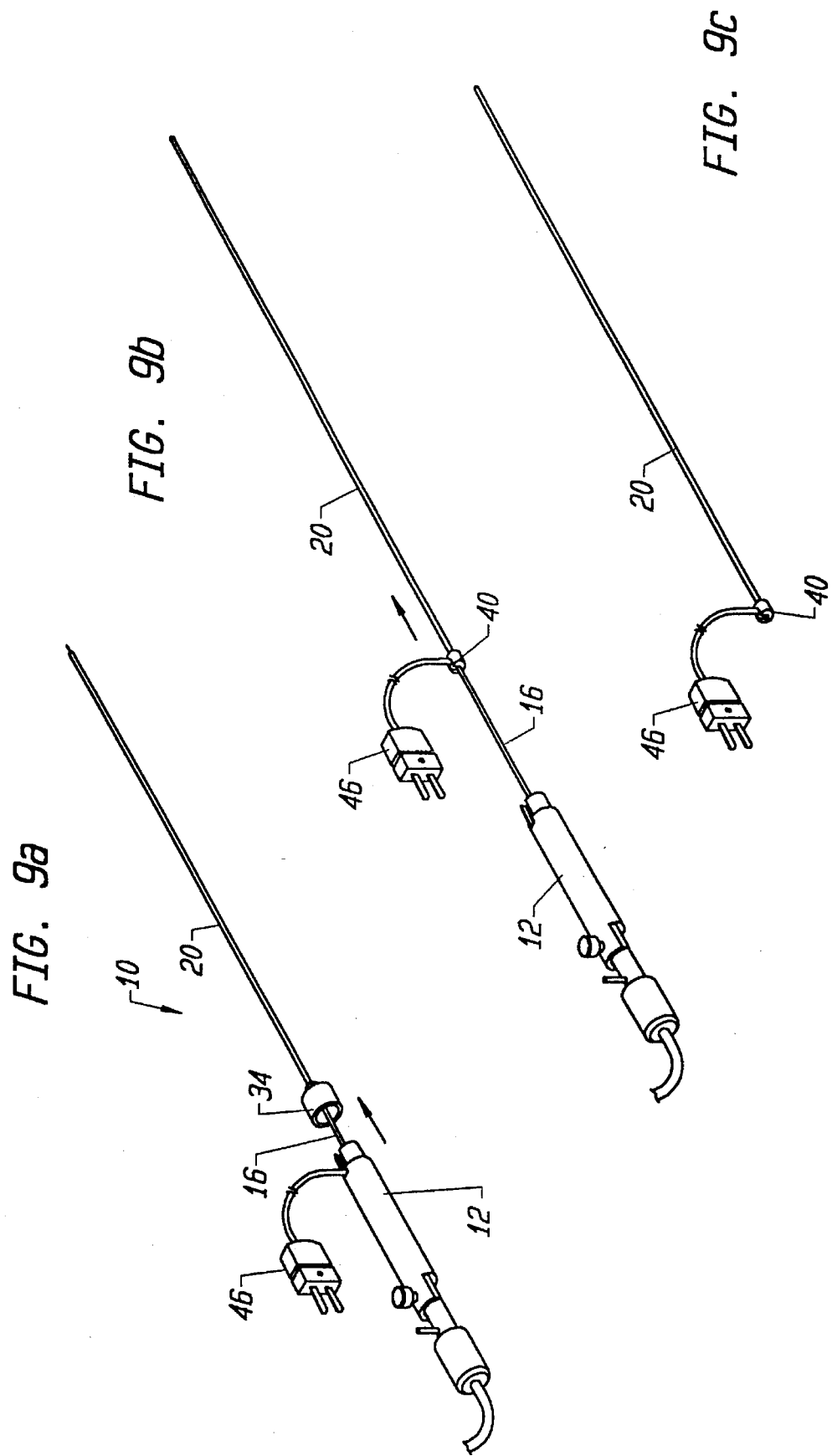

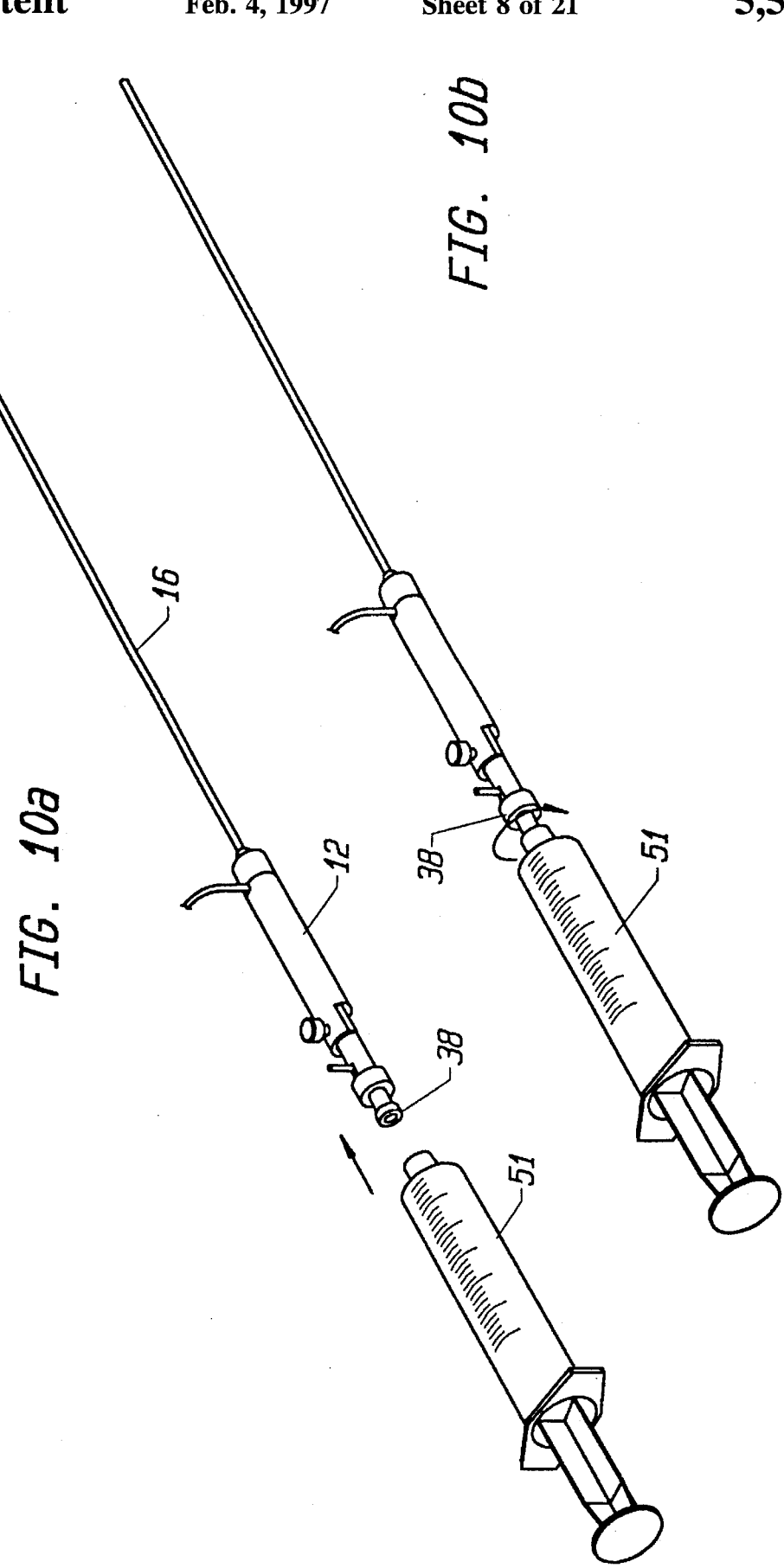

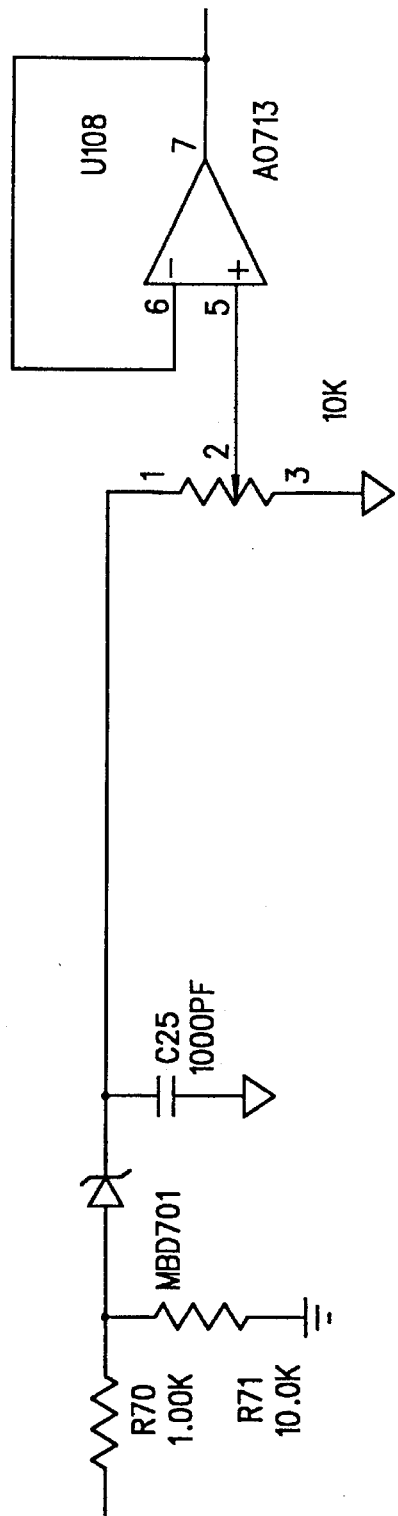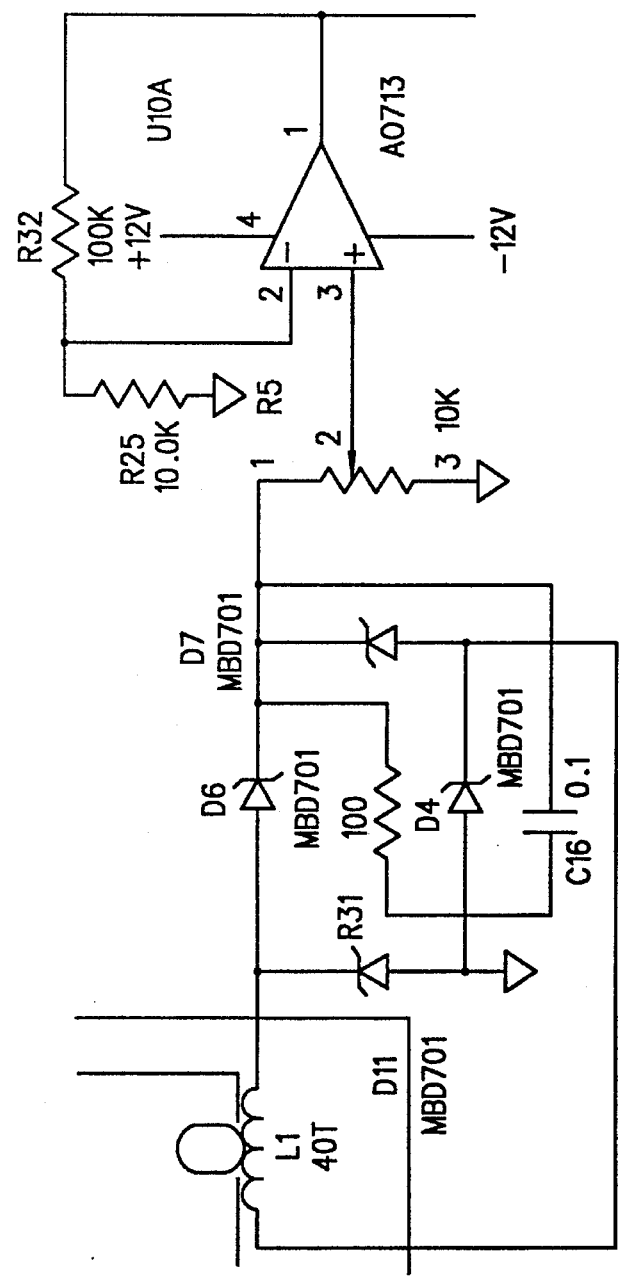
FIG. 12b
FIG. 12c

RF TREATMENT SYSTEM

CONTINUING APPLICATION DATA

This application is a continuation-in-part of U.S. patent application Ser. No. 08/148,439 filed Nov. 8, 1993, now U.S. Pat. No. 5,458,597, entitled "DEVICE FOR TREATING CANCER AND NON-MALIGNANT TUMORS AND METHODS", by Edwards et al. which is incorporated herein by reference.

BACKGROUND OF THE INVENTION

1. Field of the Invention

This invention relates generally to an apparatus for the treatment and ablation of body masses, such as tumors, and more particularly, to an RF treatment system suitable for multi-modality treatment with an infusion delivery device, catheter, removable electrode, insulator sleeve and introducer, all housed in the catheter. The system maintains a selected power at an electrode what is independent of changes in current or voltage.

2. Description of the Related Art

Current open procedures for treatment of tumors are extremely disruptive and cause a great deal of damage to healthy tissue. During the surgical procedure, the physician must exercise care in not cutting the tumor in a manor that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the body. Certain techniques have been developed with microwave radiation and ultrasound to focus energy at various desired depths. RF applications may be used at depth during surgery. However, the extent of localization is generally poor, with the result that healthy tissue may be harmed. Induction heating gives rise to poor localization of the incident energy as well. Although induction heating may be achieved by placing an antenna on the surface of the body, superficial eddy currents are generated in the immediate vicinity of the antenna, when it is driven using RF current, and unwanted surface heating occurs with little heating delivered to the underlying tissue.

Thus, non-invasive procedures for providing heat to internal tumors have had difficulties in achieving substantial specific and selective treatment.

Hyperthermia, which can be produced from an RF or microwave source, applies heat to tissue but does not exceed 45 degrees C. so that normal cells survive. In thermotherapy, heat energy of greater than 45 degrees C. is applied, resulting in histological damage, desiccation and the denaturization of proteins. Hyperthermia has been applied more recently for therapy of malignant tumors. In hyperthermia, it is desirable to induce a state of hyperthermia that is localized by interstitial current heating to a specific area while concurrently insuring minimum thermal damage to healthy surrounding tissue. Often, the tumor is located subcutaneously and addressing the tumor requires either surgery, endoscopic procedures or external radiation. It is difficult to externally induce hyperthermia in deep body tissue because current density is diluted due to its absorption by healthy tissue. Additionally, a portion of the RF energy is reflected at the muscle/fat and bone interfaces which adds to the problem of depositing a known quantity of energy directly on a small tumor.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

There have been a number of different treatment methods and devices for minimally invasively treating tumors. One such example is an endoscope that produces RF hyperthermia in tumors, as disclosed in U.S. Pat. No. 4,920,978. A microwave endoscope device is described in U.S. Pat. No. 4,409,993. In U.S. Pat. No. 4,920,978, an endoscope for RF hyperthermia is disclosed.

In U.S. Pat. No. 4,763,671 (the "'671 patent"), a minimally invasive procedure utilizes two catheters that are inserted interstitially into the tumor. The catheter includes a hard plastic support member. Around the support member is a conductor in the form of an open mesh. A layer of insulation is secured to the conductor with adhesive beads. It covers all of the conductor except a preselected length which is not adjustable. Different size tumors can not be treated with the same electrode. A tubular sleeve is introduced into the support member and houses radioactive seeds. The device of the '671 patent fails to provide for the introduction of a fluidic medium, such as a chemotherapeutic agent, to the tumor for improved treatment. The size of the electrode conductive surface is not variable. Additionally, the device of the '671 patent is not capable of maintaining a preselected level of power that is independent of changes in voltage or current.

In U.S. Pat. No. 4,565,200 (the "'200 patent"), an electrode system is described in which a single entrance tract cannula is used to introduce an electrode into a selected body site. The device of the '200 patent is limited in that the single entrance tract fails to provide for the introduction, and removal of a variety of inserts, including but not limited to an introducer, fluid infusion device and insulation sleeve. Additionally, the device of the '200 patent fails to provide for the maintenance of a selected power independent of changes in current or voltage.

There is a need for an RF treatment system which provides bipolar ablation between two or more electrodes, with a deflectable introducer that is advanced out of the distal end of at least one of the electrodes and is able to determine the temperature of the tissue in an ablation volume created by the bipolar ablation of the electrodes. It would be desirable to provide an RF treatment system with two or more electrodes operating in a bipolar mode to create an ablation volume, and at least one of the electrodes has an electrode extension which is laterally deflectable at its distal end to provide the additional capability of monopolar ablation.

SUMMARY

Accordingly, an object of the invention is to provide an RF treatment system which provides bipolar ablation between two or more electrodes to create an ablation volume, and a the temperature substantially anywhere in the ablation volume can be measured to determine the extent of ablation.

Another object of the invention is to provide an RF treatment system which has at least two needle electrodes positioned in respective catheters, and a deflectable introducer is introduced through a distal end of one of the catheters to measure temperature in the ablation volume.

Still a further object of the invention is to provide an RF treatment system with two or more needle electrodes positioned in respective catheters that provide bipolar ablation defining an ablation volume, and subsequent monopolar ablation. A first needle extension is positioned at a distal end of one of the two needle electrodes and has a deflectable distal end that provides monopolar ablation.

Yet another object of the invention is to provide an RF treatment system with two or more needle electrodes positioned in respective catheters that provide bipolar ablation defining an ablation volume. A first needle extension is positioned at a distal end of one of the two needle electrodes and has a deflectable distal end that provides monopolar ablation.

Another object of the invention is to provide an RF treatment system which includes a at least two needle electrodes for bipolar ablation to create an ablation volume. A selected power is maintained at the electrodes independent of changes in voltage or current.

A further object of the invention is to provide an RF treatment system including at least two electrodes providing bipolar ablation and further including an infusion device associated with at least one of the electrodes.

Another object of the invention is to provide an RF treatment system including at least two electrodes providing bipolar ablation and further including an infusion device associated with at least one of the electrodes. The electrodes are removable from the infusion device which can remain positioned in a body structure to permit the introduction of a chemotherapeutic agent directly through the infusion device, or through a separate delivery device positioned in the lumen of the infusion device.

These and other objects of the invention are achieved with an RF treatment system that includes a first catheter including a first catheter lumen and a first catheter distal end. A first needle electrode, including a first needle electrode lumen and a first needle electrode distal end, is at least partially positioned in the first catheter lumen. A first insulator sleeve is in a slideable surrounding relationship to the first needle electrode and defines a first needle ablation surface. A second catheter is includes and has a second catheter lumen and a second catheter distal end. A second needle electrode, including a second needle electrode lumen and a second needle electrode distal end, is at least partially positioned in the second catheter lumen. A second insulator sleeve is in a slideable surrounding relationship to the second needle electrode and defines a second needle ablation surface. An RF power source is coupled to the first and second needle electrodes. The needle electrodes provide bipolar RF ablation and define an ablation volume. A deflectable introducer has a laterally deflectable distal end. An ablation volume temperature sensor is positioned at the deflectable introducer distal end. The deflectable introducer distal end is advanced out of the distal end of the first or second needle electrodes to measure a temperature of tissue in the ablation volume.

In another embodiment of the invention, the RF treatment system includes a first catheter including a first catheter lumen and a first catheter distal end. A first needle electrode, including a first needle electrode lumen and a first needle electrode distal end, is at least partially positioned in the first catheter lumen. A first insulator sleeve is in a slideable surrounding relationship with the first needle electrode and defines a first needle ablation surface. A second catheter includes a second catheter lumen and a second catheter distal end. A second needle electrode, with a second needle electrode lumen and a second needle electrode distal end, is at least partially positioned in the second catheter lumen. A second insulator sleeve is in a slideable surrounding relationship to the second electrode and defines a second needle ablation surface. An RF power source is coupled to the first and second needle electrodes, with the first and second needle electrodes providing bipolar RF ablation between them in an ablation volume. A first needle extension is provided with a laterally deflectable distal end. The first needle extension is positioned at the distal end of the first needle electrode, coupled to the RF power source and advanced in and out of the distal end of the first needle electrode to provide monopolar ablation.

Further, resources are coupled to the electrodes and the RF power supply to maintain a selected power at the electrodes which is independent of changes in voltage or current. First and second removeable introducers can be positioned in the lumens of the first and second needle electrodes respectively. Each introducer can include a sensor positioned on a surface of the introducer. Sensors can also be includes on the surfaces of the first and second insulator sleeves. The resources can also be coupled to these sensors.

Infusion devices can be associated with one or more of the catheters. Following ablation, the electrodes and catheters can be removed from the infusion devices. A source of an infusion media, including but not limited to a chemotherapeutic agent, can then be introduced through the infusion devices. Following the introduction of the infusion media, the catheters and electrodes can be reintroduced through the infusion devices and further ablation can be conducted. Additionally, the electrodes can be hollow and include fluid distribution ports. Infusion media can be introduced through the electrodes before, during and after ablation.

The system of the invention provides for the bipolar ablation of a tumor or selected mass between two or more needle electrodes. An introducer, with a deflectable distal end, can be advanced in and out of a distal end of one or more of the electrodes in order to measure temperature of tissue in an ablation volume. In this manner, the physician is able to determine the extent of ablation, and whether or not it is completed. The introducer's distal end is laterally deflected or deflectable so that the entire ablation volume can be measured. The introducer's distal end can be made of a memory metal.

Additionally, the system of the invention includes a needle electrode extension associated with one or more of the needle electrodes of the system. Each needle electrode extension has a laterally deflectable distal end that provides monopolar ablation. This is particularly useful for difficult to access areas, or at locations where there are vessels and other structures that should not be ablated. Thus, the system of the invention provides for bipolar ablation for two or more needle electrodes, as well as monopolar ablation for difficult to access area s.

DESCRIPTION OF THE DRAWINGS

FIG. 1(a) is a cross-sectional view of an RF treatment apparatus of the invention.

FIG. 1(b) is a close up cross-sectional view of the distal end of the RF treatment apparatus of FIG. 1(a).

FIG. 1(c) is a close up cross-sectional view of the RF treatment apparatus of FIG. 1(a), illustrating the proximal end of the insulation sleeve and a thermocouple associated with the insulation sleeve.

FIG. 1(d) is a close up cross-sectional view of the RF treatment apparatus of FIG. 1(a), illustrating the proximal end of the RF treatment apparatus of FIG. 1(a).

FIG. 6(a) is a perspective view of the RF treatment apparatus of the invention with the infusion device mounted at the distal end of the catheter.

FIG. 6(b) is a perspective view of the RF treatment apparatus of FIG. 6(a) illustrating the removal of the catheter, and electrode attached to the distal end of the electrode, from the infusion device which is left remaining in the body.

FIG. 7(a) is a perspective view of the RF treatment apparatus of the invention with the electrode mounted at the distal end of the catheter.

FIG. 7(b) is a perspective view of the RF treatment apparatus of FIG. 7(a) illustrating the removal of the introducer from the lumen of the electrode.

FIG. 8(a) is a perspective view of the RF treatment apparatus of the invention with the introducer removed from the lumen of the electrode.

FIG. 8(b) is a perspective view of the apparatus of FIG. 8(a) illustrating the removal of the electrode from the catheter, leaving behind the insulation sleeve.

FIG. 9(a) is a perspective view of the RF ablation apparatus of the invention with the insulation sleeve positioned in a surrounding relationship to the electrode which is mounted to the distal end of the catheter.

FIG. 9(b) is a perspective view of the RF ablation apparatus of FIG. 9(a) illustrating the removal of the insulation sleeve from the electrode.

FIG. 9(c) is a perspective view of the insulation sleeve after it is removed from the electrode.

FIG. 10(a) is a perspective view illustrating the attachment of a syringe to the device of FIG. 8(a).

FIG. 10(b) is a perspective view of a syringe, containing a fluid medium such as a chemotherapeutic agent, attached to the RF ablation apparatus of FIG. 8(a).

FIG. 12(b) is a schematic diagram of a voltage sensor suitable useful with the invention.

FIG. 12(c) is a schematic diagram of a current sensor suitable useful with the invention.

DETAILED DESCRIPTION OF THE PREFERRED EMBODIMENTS

Figure 2:
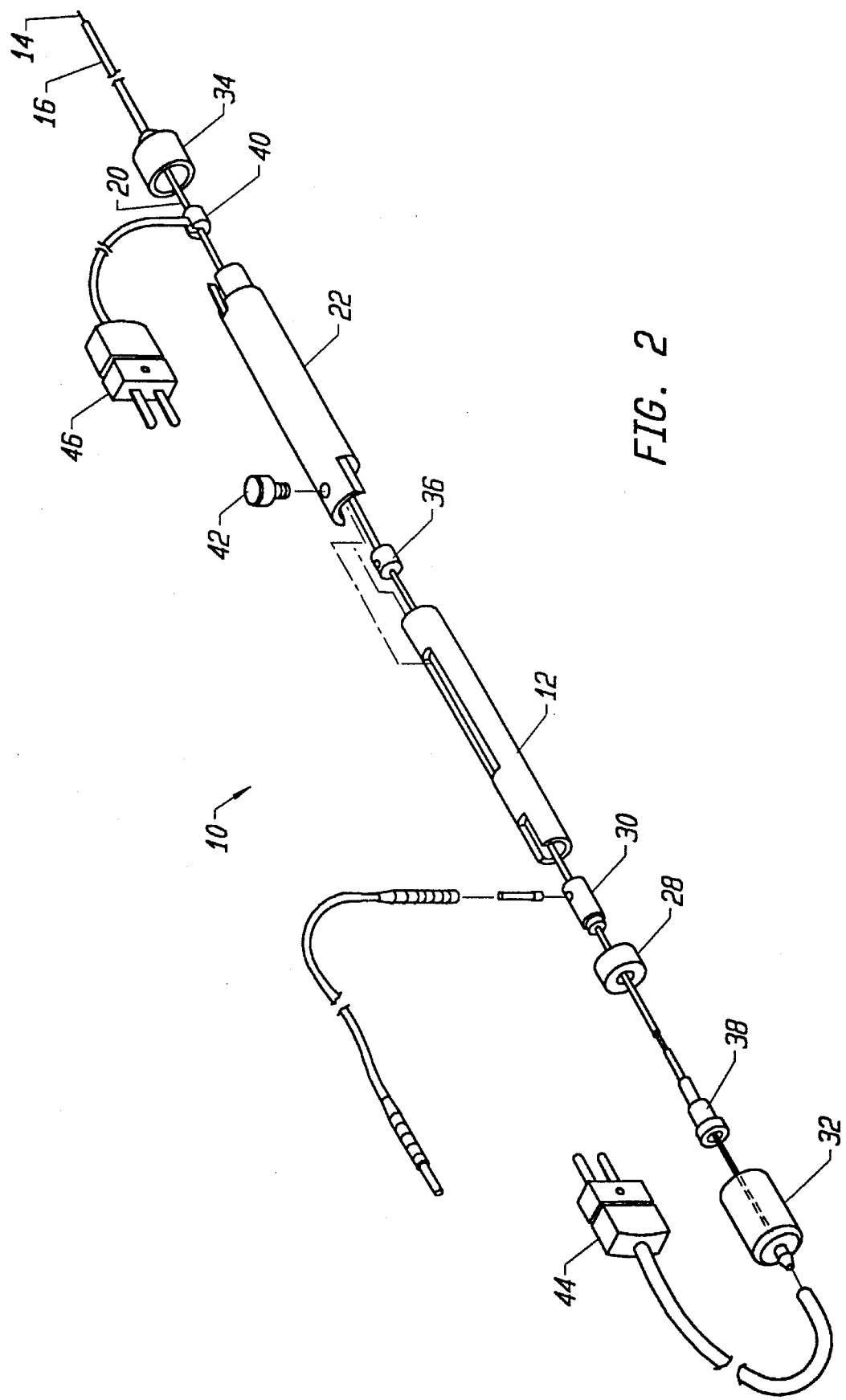
FIG. 2 is an exploded view of an RF treatment apparatus of the invention.
Figure 3:
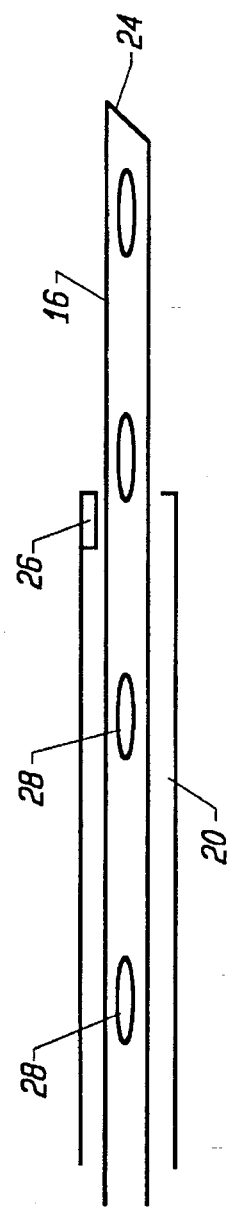
FIG. 3 is a cross-sectional view of the RF treatment apparatus of the invention illustrating the electrode, insulation sleeve and the associated thermal sensors.

Referring now to FIGS. 1(a). 1(b), 1(c), 2 and 3 an RF treatment apparatus 10 is illustrated which can be used to ablate a selected tissue mass, including but not limited to a tumor, or treat the mass by hyperthermia. Treatment apparatus 10 includes a catheter 12 with a catheter lumen in which different devices are introduced and removed. An insert 14 is removably positioned in the catheter lumen. Insert 14 can be an introducer, a needle electrode, and the like.

When insert 14 is an introducer, including but not limited to a guiding or delivery catheter, it is used as a means for puncturing the skin of the body, and advancing catheter 12 to a desired site. Alternatively, insert 14 can be both an introducer and an electrode adapted to receive RF current for tissue ablation and hyperthermia.

If insert 14 is not an electrode, then a removable electrode 16 is positioned in insert 14 either during or after treatment apparatus 10 has been introduced percutaneously to the desired tissue site. Electrode 16 has an electrode distal end that advances out of an insert distal end. In this deployed position, RF energy is introduced to the tissue site along a conductive surface of electrode 16.

Electrode 16 can be included in treatment apparatus 10, and positioned within insert 14, while treatment apparatus 10 is being introduced to the desired tissue site. The distal end of electrode 16 can have substantially the same geometry as the distal end of insert 14 so that the two ends are essentially flush. Distal end of electrode 16, when positioned in insert 14 as it is introduced through the body, serves to block material from entering the lumen of insert 14. The distal end of electrode 16 essentially can provide a plug type of function.

Electrode 16 is then advanced out of a distal end of insert 14, and the length of an electrode conductive surface is defined, as explained further in this specification. Electrode 16 can advance out straight, laterally or in a curved manner out of distal end of insert 14. Ablative or hyperthermia treatment begins when two electrodes 16 are positioned closely enough to effect bipolar treatment of the desired tissue site or tumor. A return electrode attaches to the patients skin. Operating in a bipolar mode, selective ablation of the tumor is achieved. However, it will be appreciated that the present invention is suitable for treating, through hyperthermia or ablation, different sizes of tumors or masses. The delivery of RF energy is controlled and the power at each electrode is maintained, independent of changes in voltage or current. Energy is delivered slowly at low power. This minimizes desiccation of the tissue adjacent to the electrodes 16, permitting a wider area of even ablation. In one embodiment, 8 to 14 W of RF energy is applied in a bipolar mode for 10 to 25 minutes. An ablation area between electrodes 16 of about 2 to 6 cm is achieved.

Treatment apparatus 10 can also include a removable introducer 18 which is positioned in the insert lumen instead of electrode 16. Introducer 18 has an introducer distal end that also serves as a plug, to minimize the entrance of material into the insert distal end as it advances through a body structure. Introducer 18 is initially included in treatment apparatus, and is housed in the lumen of insert 14, to assist the introduction of treatment apparatus 10 to the desired tissue site. Once treatment apparatus 10 is at the desired tissue site, then introducer 18 is removed from the insert lumen, and electrode 16 is substituted in its place. In this regard, introducer 18 and electrode 16 are removable to and from insert 14.

Also included is an insulator sleeve 20 coupled to an insulator slide 22. Insulator sleeve 20 is positioned in a surrounding relationship to electrode 16. Insulator slide 22 imparts a slidable movement of the insulator sleeve along a longitudinal axis of electrode 16 in order to define an electrode conductive surface what begins at an insulator sleeve distal end.

A thermal sensor 24 can be positioned in or on electrode 16 or introducer 18. A thermal sensor 26 is positioned on insulator sleeve 20. In one embodiment, thermal sensor 24 is located at the distal end of introducer 18, and thermal sensor 26 is located at the distal end of insulator sleeve 20, at an interior wall which defines a lumen of insulator sleeve 20. Suitable thermal sensors include a T type thermocouple with copper constantene, J type, E type, K type, thermistors, fiber optics, resistive wires, thermocouples IR detectors, and the like. It will be appreciated that sensors 24 and 26 need not be thermal sensors.

Catheter 12, insert 14, electrode 16 and introducer 18 can be made of a variety of materials. In one embodiment, catheter 12 is made of black anodized aluminum, 0.5 inch, electrode 16 is made of stainless steel, 18 gauge, introducer 18 is made of stainless steel, 21 gauge, insulator sleeve 20 is made of polyimide, deflectable introducer 17 is made of nickel titanium tubing, 0.18, and needle electrode extension 19 is made of nickel titanium wire, 0.18.

By monitoring temperature, RF power delivery can be accelerated to a predetermined or desired level. Impedance is used to monitor voltage and current. The readings of thermal sensors 24 and 26 are used to regulate voltage and current that is delivered to the tissue site. The output for these sensors is used by a controller, described further in this specification, to control the delivery of RF energy to the tissue site. Resources, which can be hardware and/or software, are associated with an RF power source, coupled to electrode 16 and the return electrode. The resources are associated with thermal sensors 24 and 25, the return electrode as well as the RF power source for maintaining a selected power at electrode 16 independent of changes in voltage or current. Thermal sensors 24 and 26 are of conventional design, including but not limited to thermistors, thermocouples, resistive wires, and the like.

Electrode 16 is preferably hollow and includes a plurality of fluid distribution ports 28 from which a variety of fluids can be introduced, including electrolytic solutions, chemotherapeutic agents, and infusion media.

A specific embodiment of the RF treatment device 10 is illustrated in FIG. 2. Included is an electrode locking cap 28, an RF coupler 30, an introducer locking cap 32, insulator slide 22, catheter body 12, insulator retainer cap 34, insulator locking sleeve 36, a luer connector 38, an insulator elbow connector 40, an insulator adjustment screw 42, a thermocouple cable 44 for thermal sensor 26, a thermocouple cable 46 for thermal sensor 24 and a luer retainer 48 for an infusion device 50.

In another embodiment of RF treatment apparatus 10, electrode 16 is directly attached to catheter 12 without insert 14. Introducer 18 is slidably positioned in the lumen of electrode 16. Insulator sleeve 20 is again positioned in a surrounding relationship to electrode 16 and is slidably moveable along its surface in order to define the conductive surface. Thermal sensors 24 and 26 are positioned at the distal ends of introducer 18 and insulator sleeve 20. Alternatively, thermal sensor 24 can be positioned on electrode 16, such as at its distal end. The distal ends of electrode 16 and introducer 18 can be sharpened and tapered. This assists in the introduction of RF treatment apparatus to the desired tissue site. Each of the two distal ends can have geometries that essentially match. Additionally, distal end of introducer 18 can an essentially solid end in order to prevent the introduction of material into the lumen of catheter 16.

In yet another embodiment of RF treatment apparatus 10, infusion device 50 remains implanted in the body after catheter 12, electrode 16 and introducer 18 are all removed. This permits a chemotherapeutic agent, or other infusion medium, to be easily introduced to the tissue site over an extended period of time without the other devices of RF treatment apparatus 10 present. These other devices, such as electrode 16, can be inserted through infusion device to the tissue site at a later time for hyperthermia or ablation purposes. Infusion device 50 has an infusion device lumen and catheter 12 is at least partially positioned in the infusion device lumen. Electrode 16 is positioned in the catheter lumen, in a fixed relationship to catheter 12, but is removable from the lumen. Insulator sleeve 20 is slidably positioned along a longitudinal axis of electrode 16. Introducer 18 is positioned in a lumen of electrode 16 and is removable therefrom. A power source is coupled to electrode 16. Resources are associated with thermal sensors 24 and 26, voltage and current sensors that are coupled to the RF power source for maintaining a selected power at electrode 16.

Figures 1, 12A:
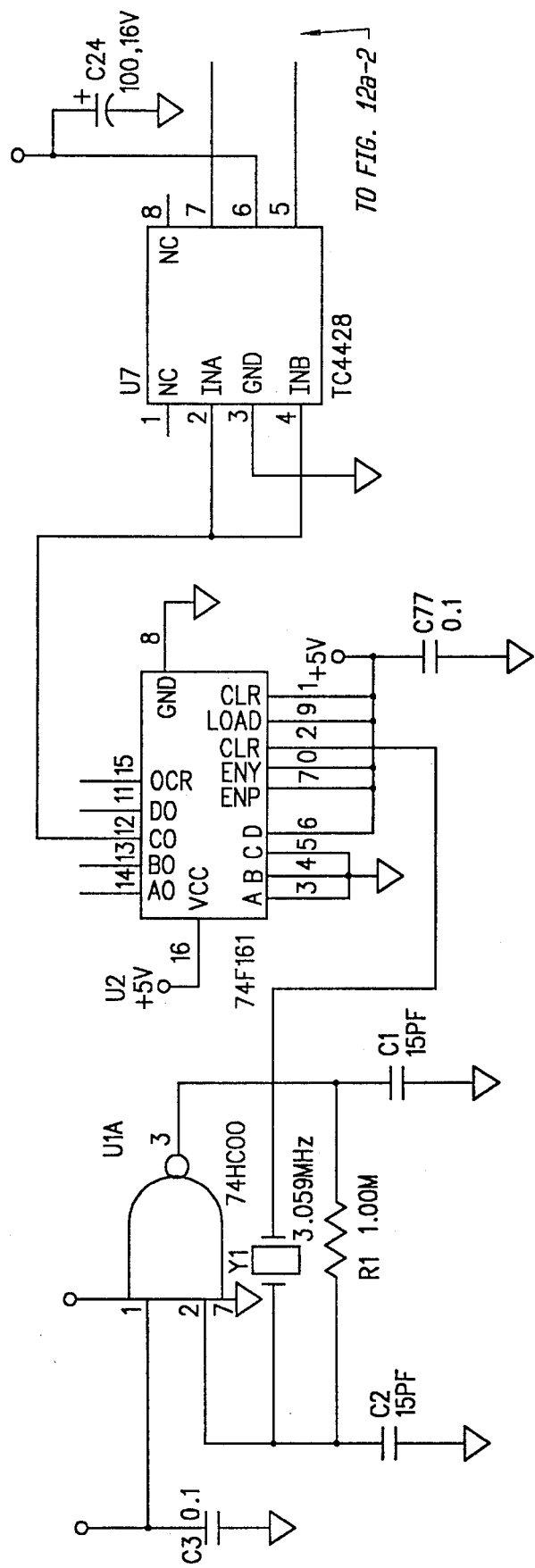
FIG. 12(a) is a schematic diagram of a power supply suitable useful with the invention.
Figures 2, 12A:
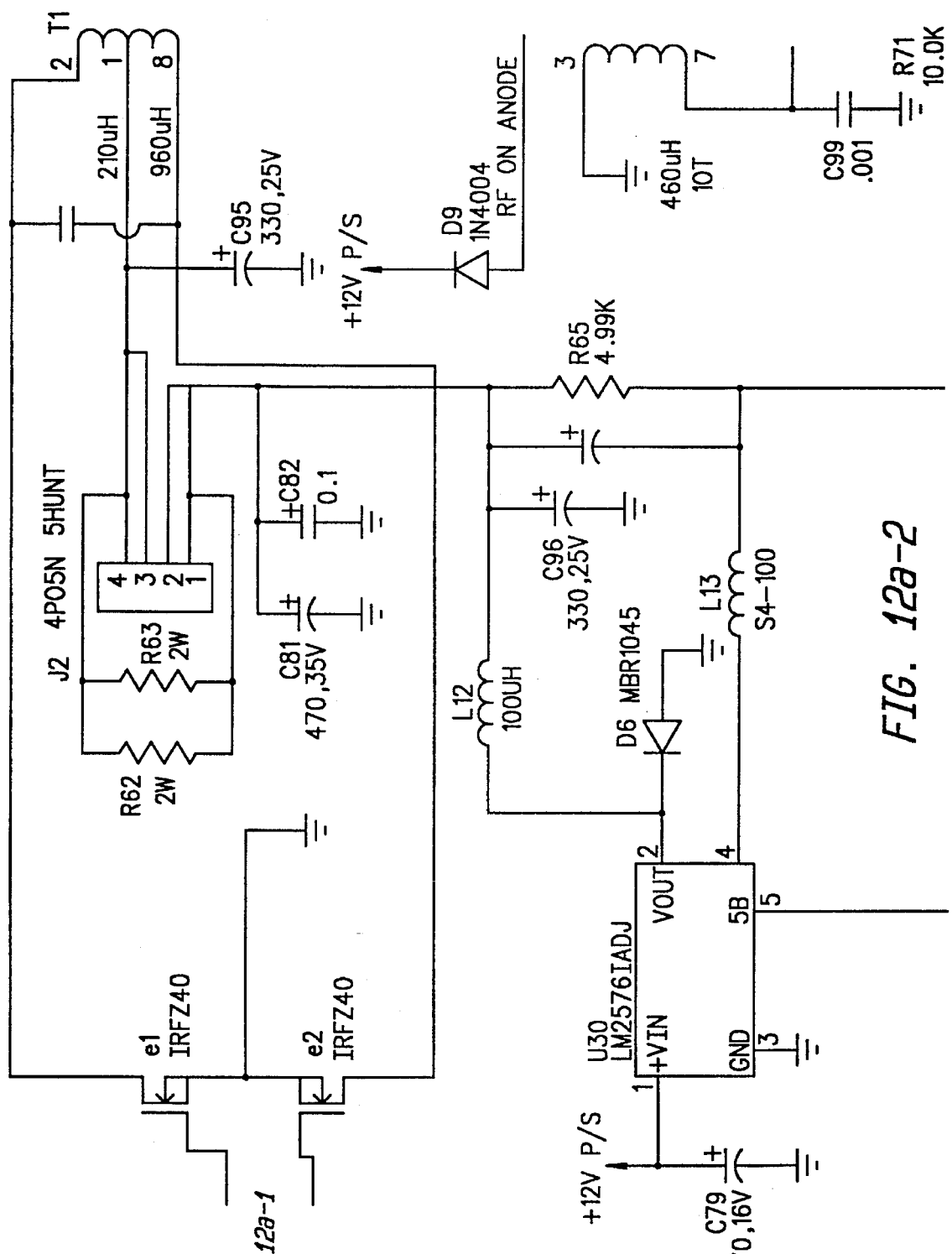
Figure 12D:
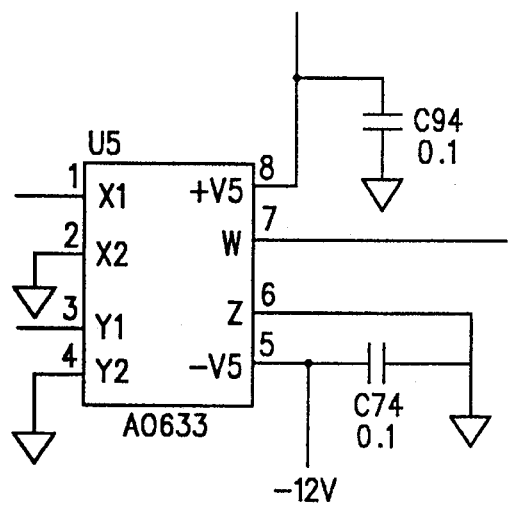
FIG. 12(d) is a schematic diagram of power computing circuits suitable useful with the invention.
Figure 12E:
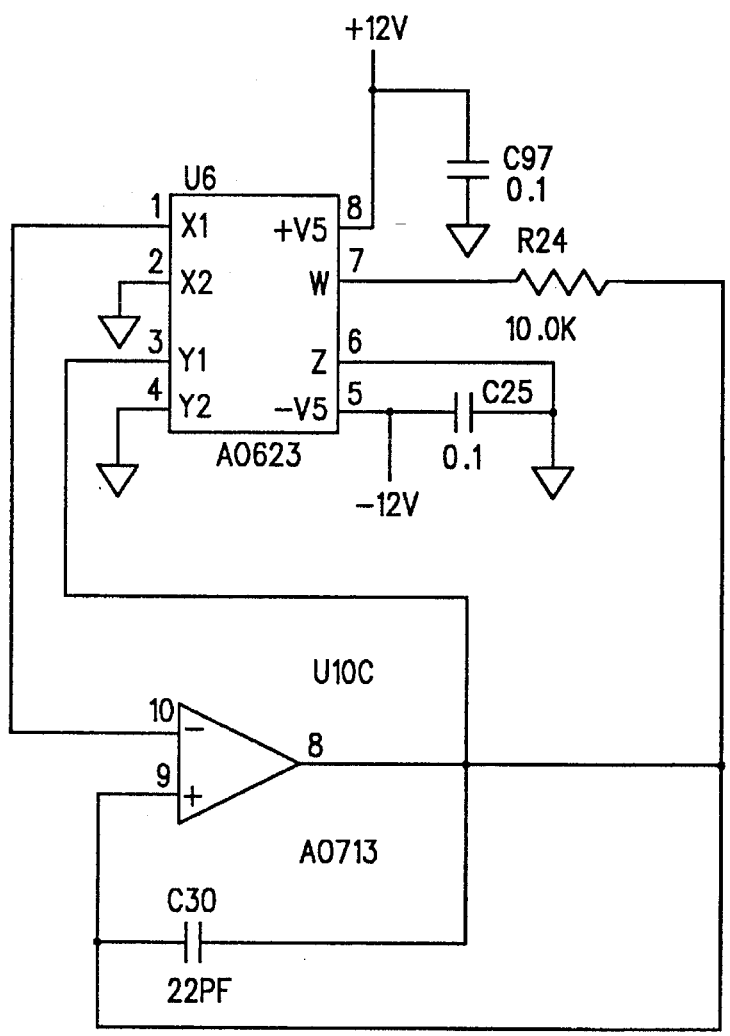
FIG. 12(e) is a schematic diagram of an impedance computing circuit suitable useful with the invention.
Figure 12F:
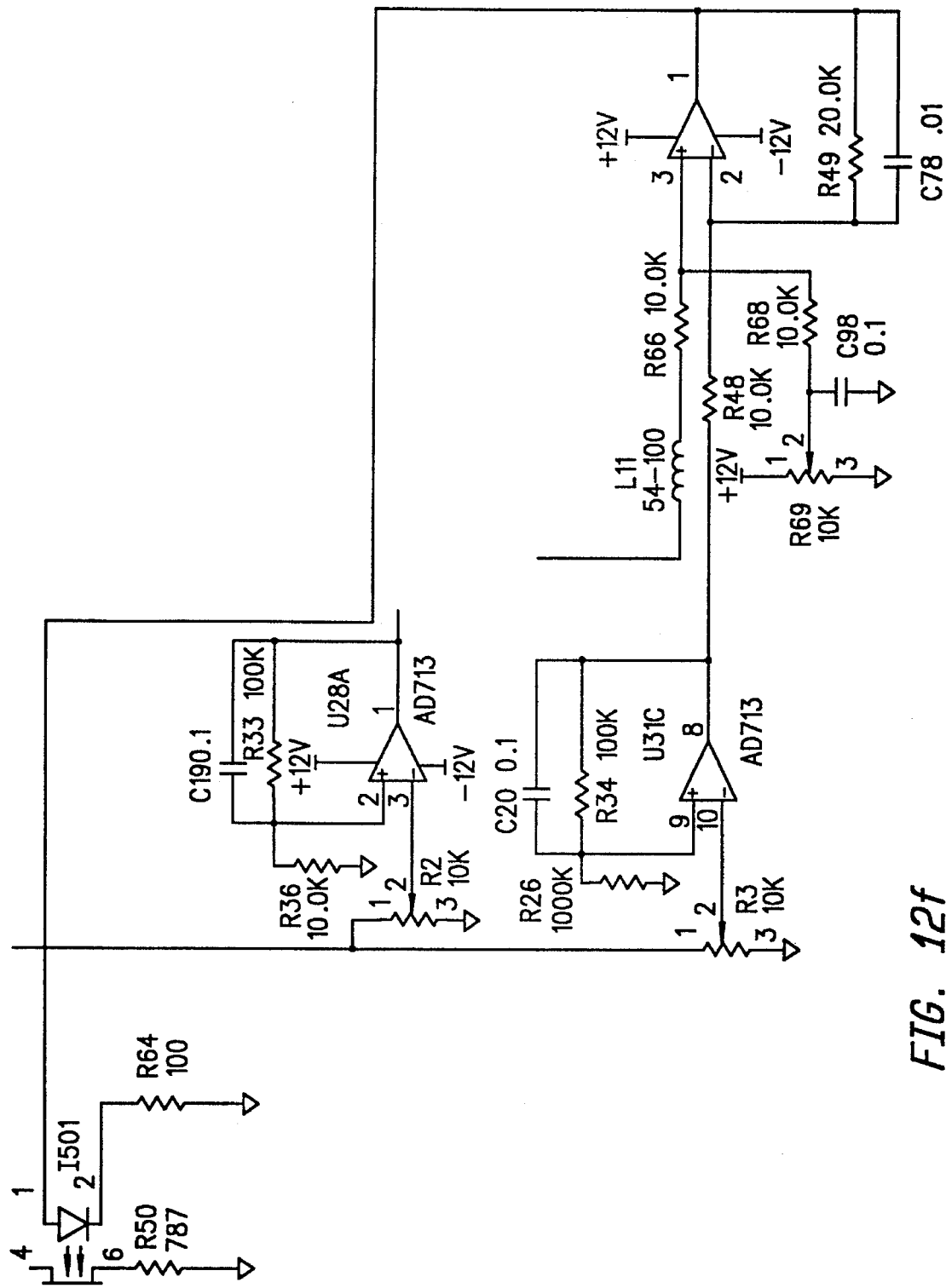
FIG. 12(f) is a schematic diagram of a power control device suitable useful with the invention.
Figures 1, 12G:
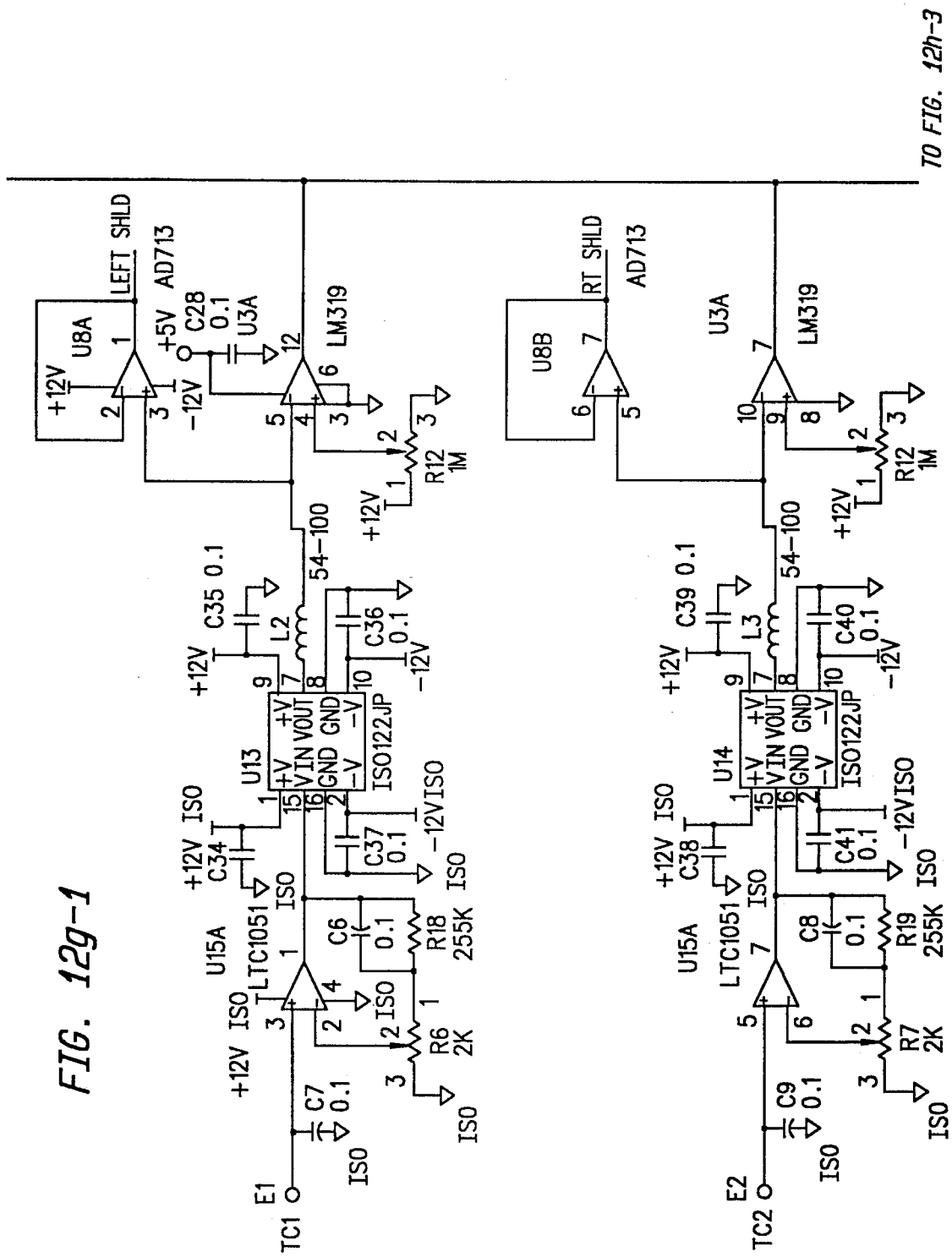
FIG. 12(g) is a schematic diagram of an eight channel temperature measurement suitable useful with the invention.
Figures 2, 12G:
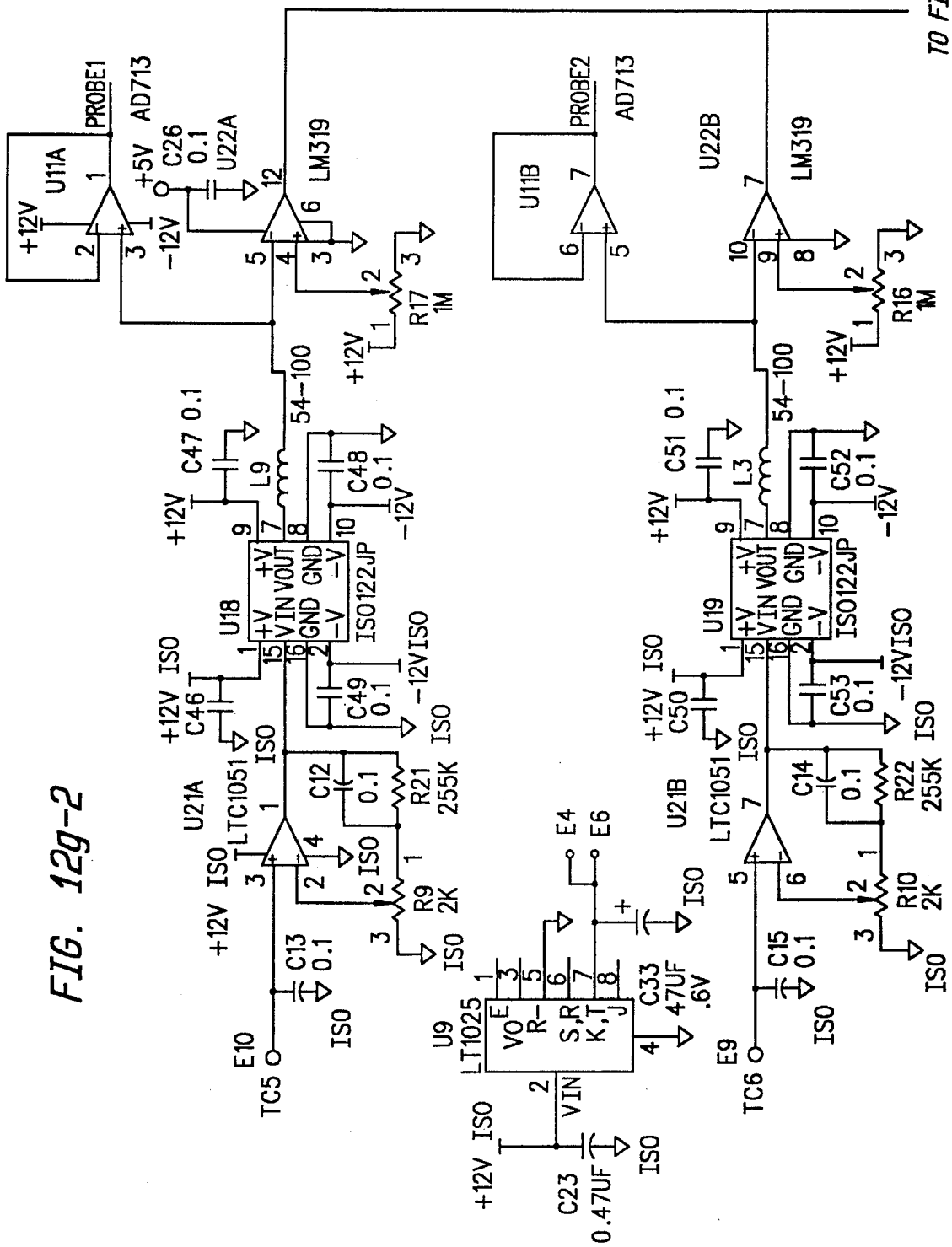
Figures 3, 12G:
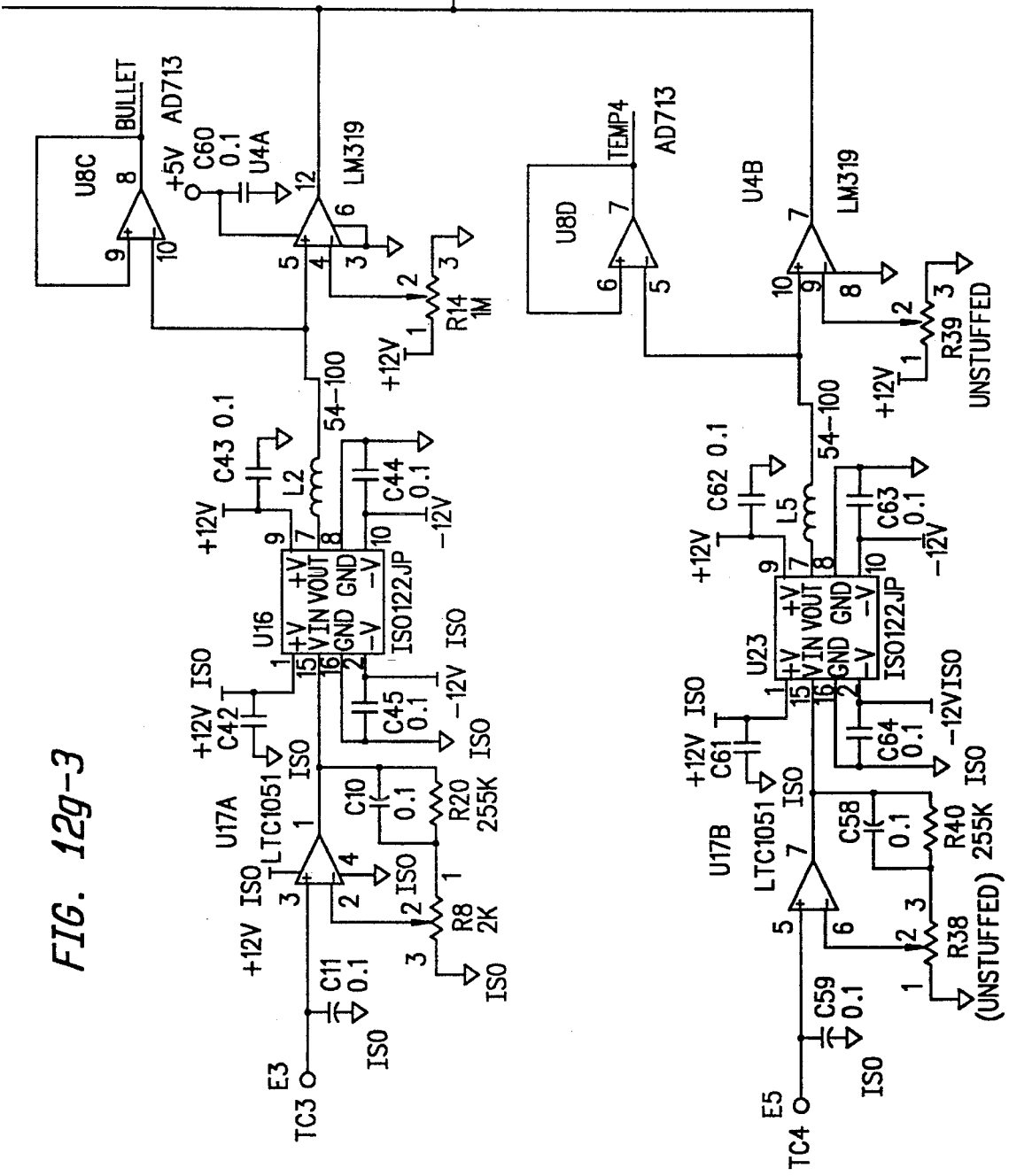
Figures 4, 12G:
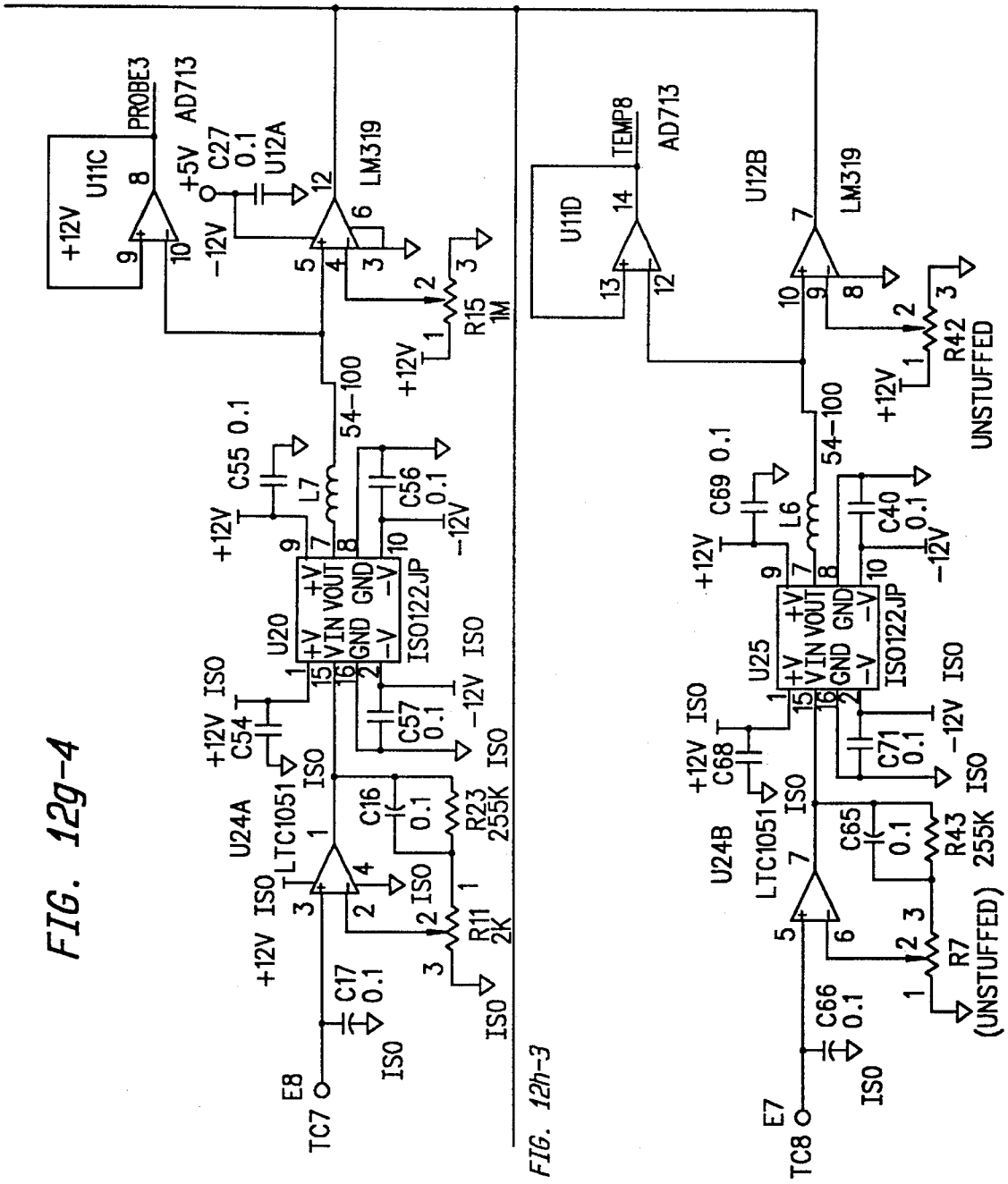
Figures 1, 12H:
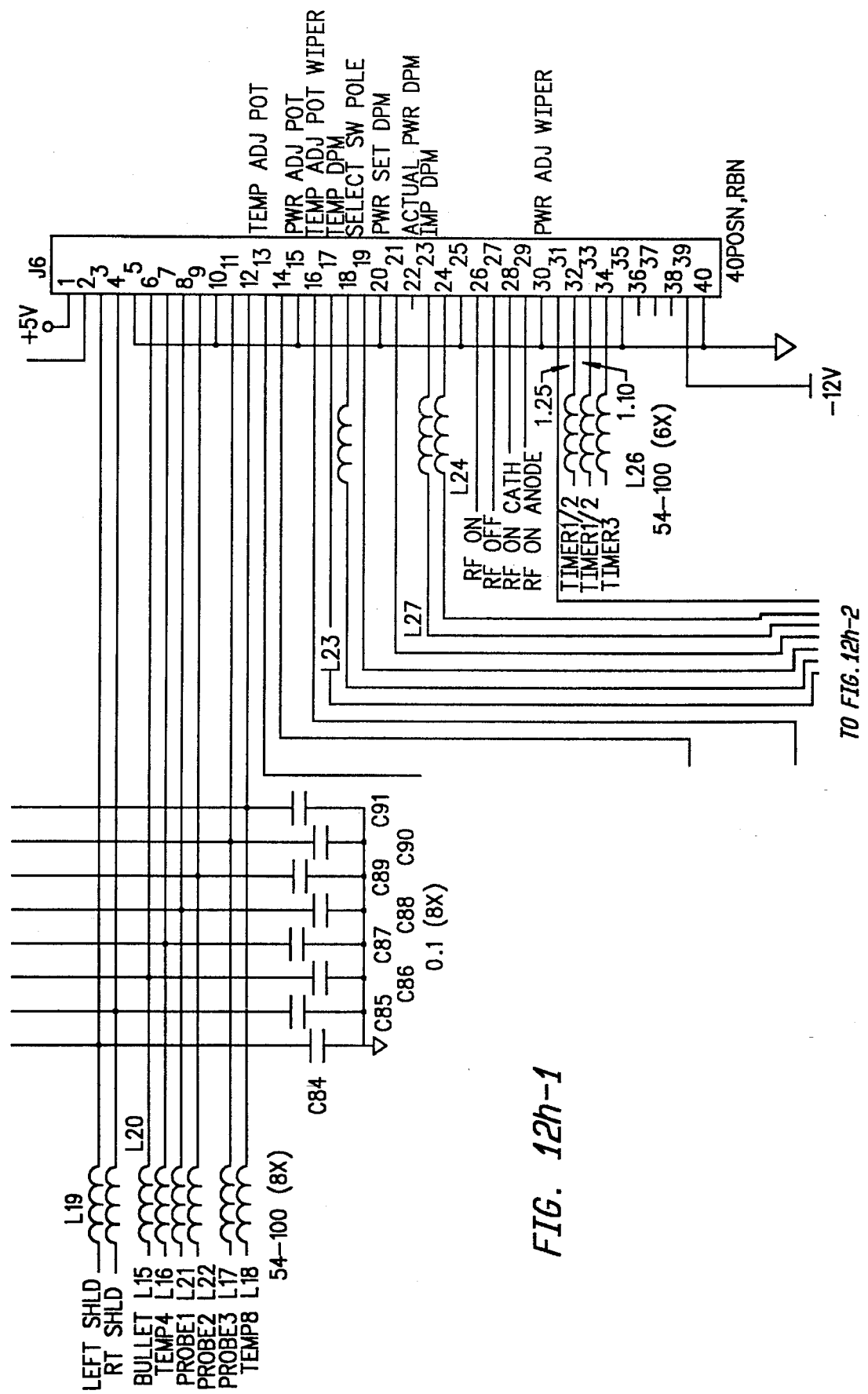
FIG. 12(h) is a schematic diagram of a power and temperature control circuit useful with the invention.
Figures 2, 12H:
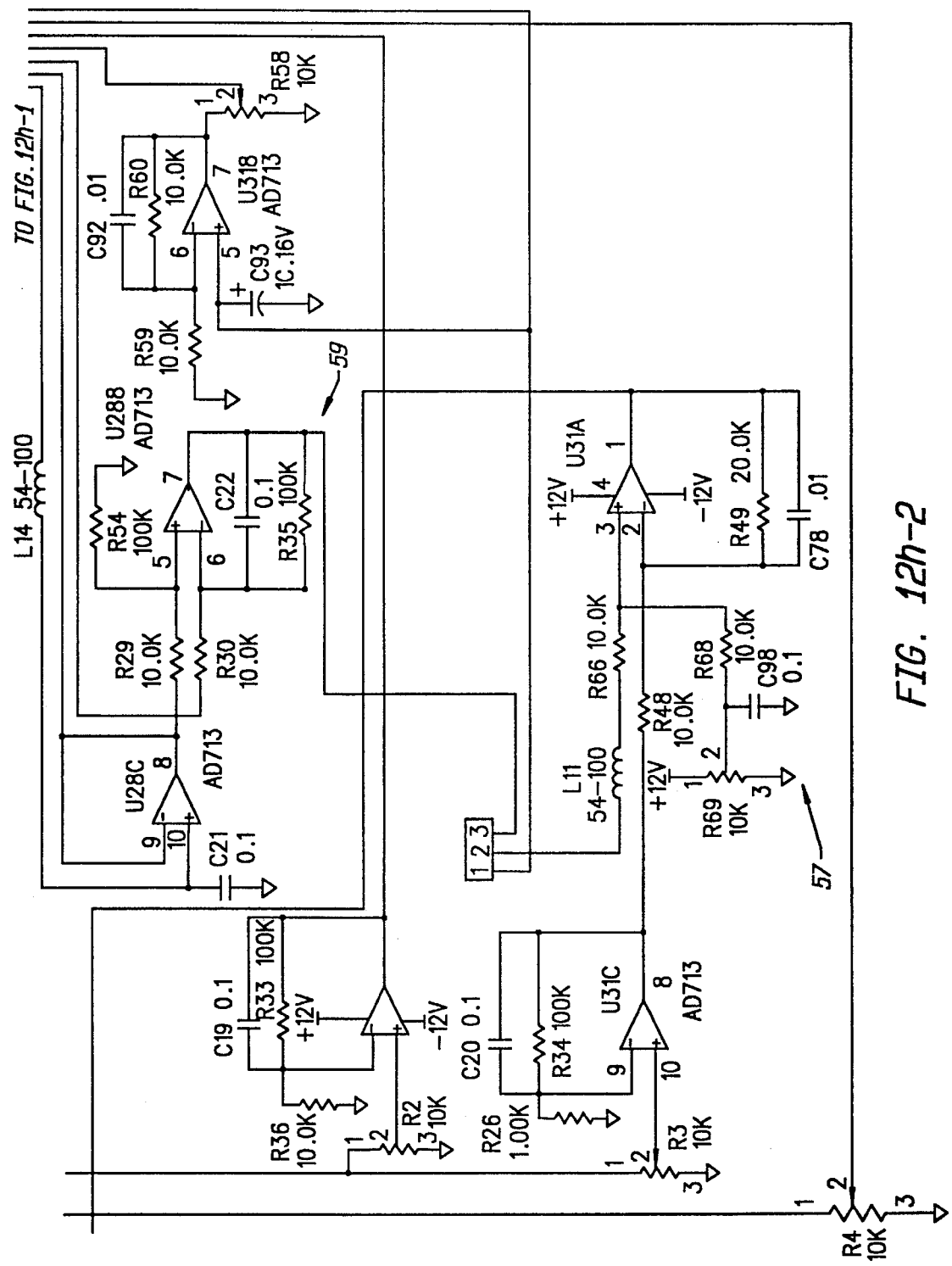

The distal end of RF treatment apparatus 10 is shown in FIG. 1(*b*). Introducer 18 is positioned in the lumen of electrode 16, which can be surrounded by insulator sleeve 20, all of which are essentially placed in the lumen of infusion device 50. It will be appreciated, however, that in FIG. 1(*b*) insert 14 can take the place of electrode 16, and electrode 16 can be substituted for introducer 18.

The distal end of insulator sleeve 20 is illustrated in FIG. 1(*c*). Thermal sensor 26 is shown as being in the form of a thermocouple. In FIG. 1(*d*), thermal sensor 24 is also illustrated as a thermocouple that extends beyond a distal end of introducer 18, or alternative a distal end of electrode 16.

Figure 4:
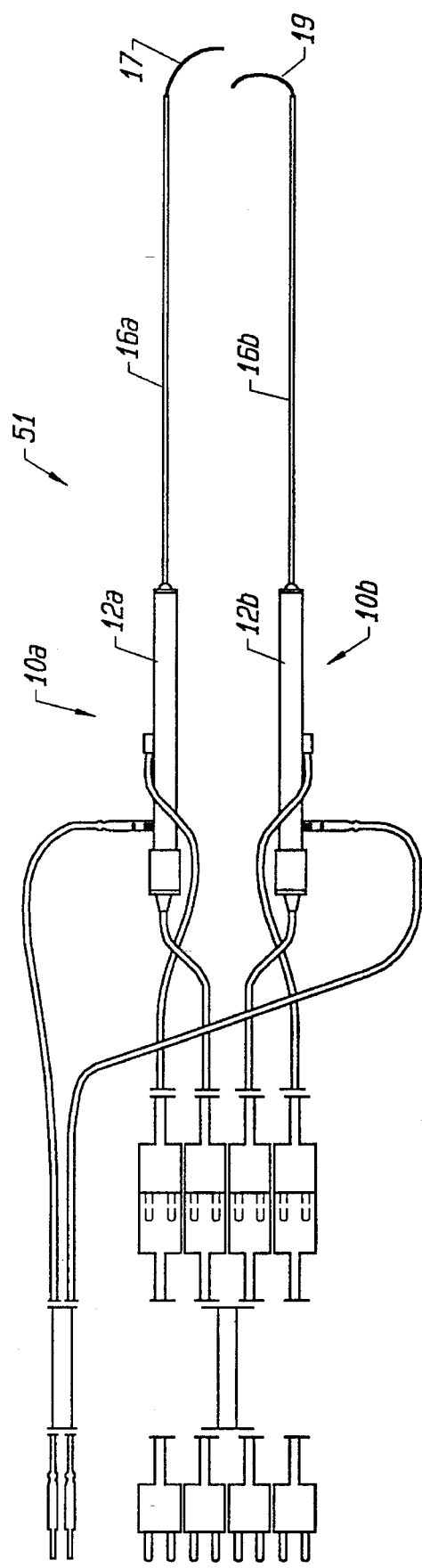
FIG. 4 is a perspective view of the RF treatment system of the invention illustrating a pair of needle electrode, with associated catheters, and RF power supply.

FIG. 4 is a perspective view of RF treatment apparatus 51 which includes a pair of RF treatment apparatus 10(*a*) and 10(*b*) respectively. RF treatment apparatus 10(*a*) includes a catheter 12(*a*), electrode 16(*a*) and a deflectable introducer 17. RF treatment apparatus 10(*b*) includes a catheter 12(*a*), electrode 16(*a*) and a needle electrode extension 19. It will be appreciated that only one of RF treatment apparatus 10(*a*) or 10(*b*) can include deflectable introducer 17 or needle electrode extension 19, each RF treatment apparatus 10(*a*) or 10(*b*) can include both, or that an RF treatment apparatus 10(*a*) or 10(*b*) can include neither. Additionally, it will be appreciated that more than one RF treatment apparatus 10 can be used with RF treatment system 51. For example, RF treatment system 51 can include three or more RF treatment apparatus, and in one embodiment two pairs of RF treatment apparatus 10 are used. Each RF treatment apparatus 10 can include deflectable introducer 17 and needle electrode extension 19.

Figure 5:
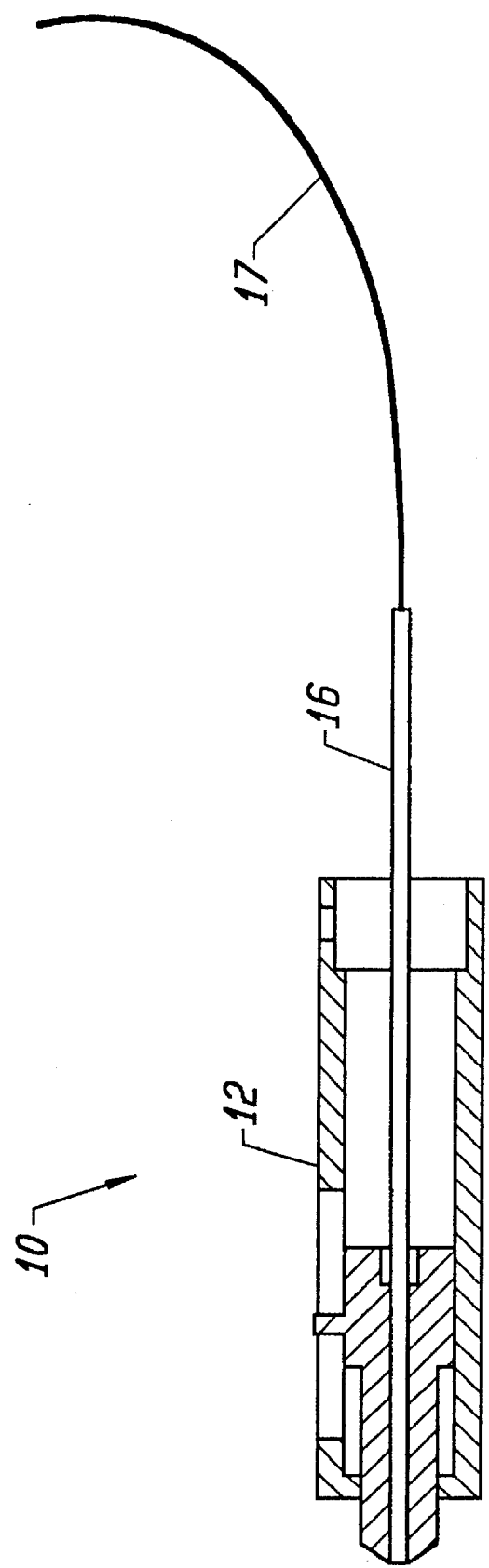
FIG. 5 is a perspective view of the RF treatment apparatus of the invention illustrating a deflectable introducer extending out of a distal end of a needle electrode.

FIG. 5 illustrates the extension of deflectable introducer 17 out of the distal end of needle electrode 16. It will be appreciated that in FIG. 5, needle electrode extension 19 can be readily substituted for deflectable introducer 17.

Deflectable introducer 17 is positioned in the lumen of needle electrode 16, or insert 14, as is advanced out its distal end. Deflectable introducer 17 includes a sensor, such as a thermal sensor, positioned at its distal end. Substantially the entire ablation volume that is created by the bipolar ablation between electrodes 16(*a*) and 16(*b*) can be measured for temperature readings, and the like. Deflectable introducer is capable of advancing through the entire ablation volume. By way of example, if a temperature of above about 75 degrees C. is measured then it is known that the tissue has received sufficient RF energy, and the ablation at that particular site is probably completed. Deflectable introducer 17 can be advanced in and out of the distal end of needle electrode 16 any number of times, and at various sites, in order to measure temperature as many times as necessary to determine that further ablation is unnecessary.

The distal end of deflectable introducer 17 must be capable of being deflectable in a lateral direction relative to a longitudinal axis of catheter 12. For this reason, the distal end of deflectable introducer 17 is made of a deflectable material including but not limited to a shaped memory metal.

A needle electrode extension 19 can be positioned at the distal end of each needle electrode 16. Needle electrode extension 19 is capable of being advanced in and out of the distal end of needle electrode 16. Additionally, the distal end of each needle electrode extension 19 is laterally deflectable with respect to a longitudinal axis of needle electrode 16.

Needle electrodes 16(*a*) and 16(*b*) preferably operate in the bipolar mode. Needle electrode extension 19 can provide monopolar ablation. This is particularly useful in tissue sites that are adjacent to organs and vessels which should not be ablated. If bipolar ablation is practiced, then there is a danger that these organs and vessels, which are not ablation targets, can become ablated. Thus, with the inclusion of needle electrode extension 19, in one or all of the needle electrodes, monopolar ablation can be achieved. It will be appreciated, however, that needle electrode extension 19 can also be operated in the bipolar mode. Thus, RF treatment system 51 can provide bipolar ablation, monopolar ablation as well as the introduction of a variety of fluid media, including but not limited to chemotherapeutic agents.

The distal end of needle electrode extension 19 is laterally deployed. It can be made of a suitable material that is capable of this lateral deployment, including but not limited to shaped memory metals and the like. Additionally, the distal end of needle electrode extension 19 can include a thermal sensor, or other type of suitable sensor desired. In one embodiment, needle electrode extension 19 is advanced out of the distal end of needle electrode 16, the temperature sensed, monopolar ablation performed, needle electrode extension 19 is then retracted back into the lumen of needle electrode 16, catheter 12 is then rotated, needle electrode extension 19 is than advanced again out of the distal end of needle electrode 16, it then can measure temperature and/or ablate, and once again be retracted. This can occur any number of times until the desired ablation effect is achieved.

The distal ends of deflectable introducer 17 and needle electrode extension 19 can be laterally deployed sufficiently to reach any place in the ablation volume created by the bipolar ablation of electrodes 16(*a*) and 16(*b*).

Referring now to FIGS. 6(*a*) and 6(*b*), infusion device 50 is attached to the distal end of catheter 12 and retained by a collar. The collar is rotated, causing catheter 12 to become disengaged from infusion device 50. Electrode 16 is attached to the distal end of catheter 12. Catheter 12 is pulled away from infusion device 50, which also removes electrode 16 from infusion device 50. Thereafter, only infusion device 50 is retained in the body. While it remains placed, chemotherapeutic agents can be introduced through infusion device 50 to treat the tumor site. Additionally, by leaving infusion device 50 in place, catheter 12 with electrode 16 can be reintroduced back into the lumen of infusion device 50 at a later time for additional RF treatment in the form of ablation or hyperthermia.

In FIG. 7(*a*), electrode 16 is shown as attached to the distal end of catheter 12. Introducer 18 is attached to introducer locking cap 32 which is rotated and pulled away from catheter 12. As shown in FIG. 7(*b*) this removes introducer 18 from the lumen of electrode 16.

Referring now to FIG. 8(*a*), electrode 16 is at least partially positioned in the lumen of catheter 12. Electrode locking cap 28 is mounted at the proximal end of catheter 12, with the proximal end of electrode 16 attaching to electrode locking cap 28. Electrode locking cap 28 is rotated and unlocks from catheter 12. In FIG. 8(*b*), electrode locking cap 28 is then pulled away from the proximal end of catheter 12, pulling with it electrode 16 which is then removed from the lumen of catheter 12. After electrode 16 is removed from catheter 12, insulator sleeve 20 is locked on catheter 12 by insulator retainer cap 34.

In FIG. 9(*a*), insulator retainer cap 34 is unlocked and removed from catheter 12. As shown in FIG. 9(*b*), insulator sleeve 20 is then slid off of electrode 16. FIG. 9(*c*) illustrates insulator sleeve 20 completely removed from catheter 12 and electrode 16.

Referring now to FIGS. 10(*a*) and 10(*b*), after introducer 18 is removed from catheter 12, a fluid source, such as syringe 51, delivering a suitable fluid, including but not limited to a chemotherapeutic agent, attaches to luer connector 38 at the proximal end of catheter 12. Chemotherapeutic agents are then delivered from syringe 51 through electrode 16 to the tumor site. Syringe 51 is then removed from catheter 12 by imparting a rotational movement of syringe 51 and pulling it away from catheter 12. Thereafter, electrode 16 can deliver further RF power to the tumor site. Additionally, electrode 16 and catheter 12 can be removed, leaving only infusion device 50 in the body. Syringe 51 can then be attached directly to infusion device 50 to introduce a chemotherapeutic agent to the tumor site. Alternatively, other fluid delivery devices can be coupled to infusion device 50 in order to have a more sustained supply of chemotherapeutic agents to the tumor site.

Once chemotherapy is completed, electrode 16 and catheter 12 can be introduced through infusion device 50. RF power is then delivered to the tumor site. The process begins again with the subsequent removal of catheter 12 and electrode 16 from infusion device 50. Chemotherapy can then begin. Once it is complete, further RF power can be delivered to the tumor site. This process can be repeated any number of times for an effective multi-modality treatment of the tumor site.

Figure 11:
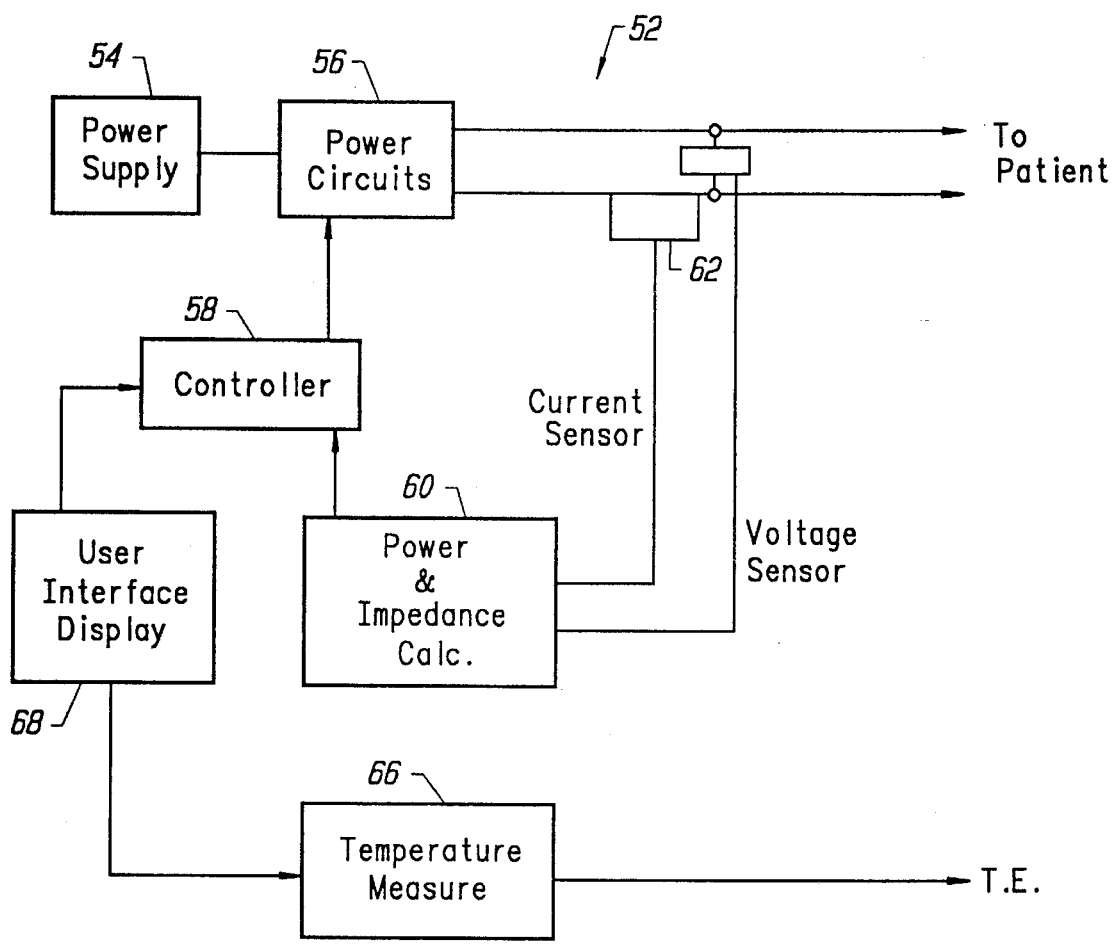
FIG. 11 is a block diagram of an RF treatment system of the invention.

Referring now to FIG. 11, a block diagram of power source 52 is illustrated. Power source 52 includes a power supply 54, power circuits 56, a controller 58, a power and impedance calculation device 60, a current sensor 62, a voltage sensor 64, a temperature measurement device 66 and a user interface and display 68.

FIGS. 12(*a*) through 12(*g*) are schematic diagrams of power supply 54, voltage sensor 64, current sensor 62, power computing circuit associated with power and impedance calculation device 60, impedance computing circuit associated with power and impedance calculation device 60, power control circuit of controller 58 and an eight channel temperature measurement circuit of temperature measure device 66, respectively.

Current delivered through each electrode 16 is measured by current sensor 62. Voltage between the electrodes 16 is measured by voltage sensor 64. Impedance and power are then calculated at power and impedance calculation device 60. These values can then be displayed at user interface 68. Signals representative of power and impedance values are received by controller 58.

A control signal is generated by controller 58 that is proportional to the difference between an actual measured value, and a desired value. The control signal is used by power circuits 56 to adjust the power output in an appropriate amount in order to maintain the desired power delivered at the respective electrode 16.

In a similar manner, temperatures detected at thermal sensors 24 and 26 provide feedback for maintaining a selected power. The actual temperatures are measured at temperature measurement device 66, and the temperatures are displayed at user interface 68. Referring now to FIG. 12(*h*), a control signal is generated by controller 59 that is proportional to the difference between an actual measured temperature, and a desired temperature. The control signal is used by power circuits 57 to adjust the power output in an appropriate amount in order to maintain the desired temperature delivered at the respective sensor 24 or 26.

Controller 58 can be a digital or analog controller, or a computer with software. When controller 58 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface 68 includes operator controls and a display. Controller 58 can be coupled to imaging systems, including but not limited to ultrasound, CT scanners and the like.

Current and voltage are used to calculate impedance. Diagnostics can be performed optically, with ultrasound, CT scanning, and the like. Diagnostics are performed either before, during and after treatment.

The output of current sensor 62 and voltage sensor 64 is used by controller 58 to maintain the selected power level at electrodes 16. The amount of RF energy delivered controls the amount of power. A profile of power delivered can be incorporated in controller 58, and a pre-set amount of energy to be delivered can also be profiled.

Circuitry, software and feedback to controller 58 result in process control, and the maintenance of the selected power that is independent of changes in voltage or current, and are used to change, (i) the selected power, including RF, ultrasound and the like, (ii) the duty cycle (on-off and wattage), (iii) bipolar energy delivery and (iv) fluid delivery, including chemotherapeutic agents, flow rate and pressure. These process variables are controlled and varied, while maintaining the desired delivery of power independent of changes in voltage or current, based on temperatures monitored at thermal sensors 24 and 26 at multiple sites.

Figure 13:
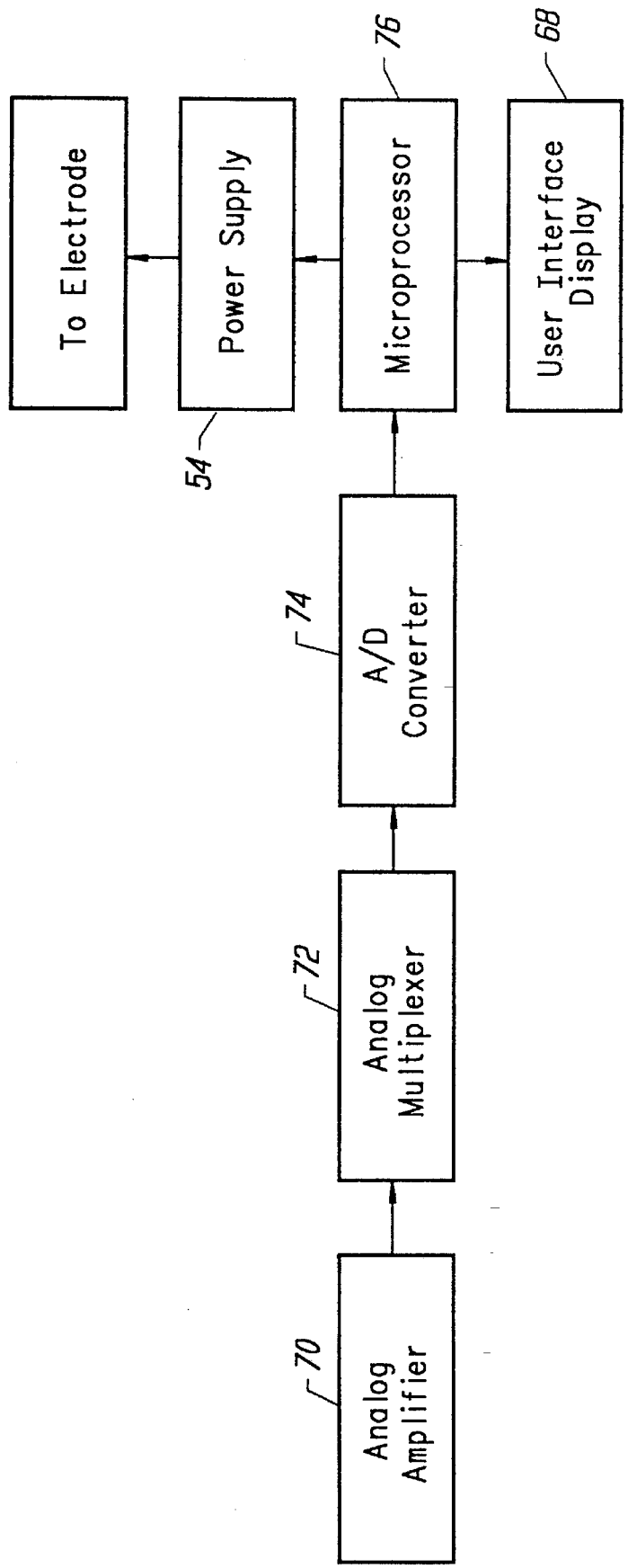
FIG. 13 is a block diagram of an embodiment of the invention which includes a microprocessor.

Controller 58 can be microprocessor controlled. Referring now to FIG. 13, current sensor 62 and voltage sensor 64 are connected to the input of an analog amplifier 70. Analog amplifier 70 can be a conventional differential amplifier circuit for use with thermal sensors 24 and 26. The output of analog amplifier 70 is sequentially connected by an analog multiplexer 72 to the input of analog-to-digital converter 74. The output of analog amplifier 70 is a voltage which represents the respective sensed temperatures. Digitized amplifier output voltages are supplied by analog-to-digital converter 74 to a microprocessor 76. Microprocessor 76 may be a type 68HCII available from Motorola. However, it will be appreciated that any suitable microprocessor or general purpose digital or analog computer can be used to calculate impedance or temperature.

Microprocessor 76 sequentially receives and stores digital representations of impedance and temperature. Each digital value received by microprocessor 76 corresponds to different temperatures and impedances.

Calculated power and impedance values can be indicated on user interface 68. Alternatively, or in addition to the numerical indication of power or impedance, calculated impedance and power values can be compared by microprocessor 76 with power and impedance limits. When the values exceed predetermined power or impedance values, a warning can be given on interface 68, and additionally, the delivery of RF energy can be reduced, modified or interrupted. A control signal from microprocessor 76 can modify the power level supplied by power supply 54.

An imaging system can be used to first define the volume of the tumor or selected mass. Suitable imaging systems include but are not limited to, ultrasound, CT scanning, X-ray film, X-ray fluoroscope, magnetic resonance imaging, electromagnetic imaging and the like. The use of such devices to define a volume of a tissue mass or a tumor is well know to those skilled in the art.

Specifically with ultrasound, an ultrasound transducer transmits ultrasound energy into a region of interest in a patient's body. The ultrasound energy is reflected by different organs and different tissue types. Reflected energy is sensed by the transducer, and the resulting electrical signal is processed to provide an image of the region of interest. In this way, the volume to be ablated is ascertained.

Ultrasound is employed to image the selected mass or tumor. This image is then imported to user interface 68. The placement of electrodes 16 can be marked, and RF energy delivered to the selected site with prior treatment planning. Ultrasound can be used for real time imaging. Tissue characterization of the imaging can be utilized to determine how much of the tissue is heated. This process can be monitored. The amount of RF power delivered is low, and the ablation or hyperthermia of the tissue is slow. Desiccation of tissue between the tissue and each needle 16 is minimized by operating at low power.

The following examples illustrate the use of the invention with two RF treatment apparatus with two electrodes, RF treatment system 51, shown in FIG. 4, or a pair of two electrodes, that are used in a bipolar mode to ablate tissue.

EXAMPLE 1

| | |
|---|---|
| Exposed electrode length: | 1.5 cm |
| Distance between electrodes: | 1.5 cm |
| Power setting: | 5 W |
| Ablation time: | 10 min. |
| Lesion size: | |
| width: | 2 cm |
| length: | 1.7 cm |
| depth: | 1.5 cm |

EXAMPLE 2

| | |
|---|---|
| Exposed electrode length: | 1.5 |
| Distance between electrodes: | 2.0 |
| Power setting: | 7.0 |
| Ablation time: | 10 min. |
| Lesion size: | |
| width: | 2.8 cm |
| length: | 2.5 cm |
| depth: | 2.2 cm |

EXAMPLE 3

| | |
|---|---|
| Exposed electrode length: | 2.5 cm |
| Distance between electrodes: | 2.0 cm |
| Power setting: | 10 W |
| Ablation time: | 10 min |
| Lesion size: | |
| width: | 3.0 cm |
| length: | 2.7 cm |
| depth: | 1.7 cm |

EXAMPLE 4

| | |
|---|---|
| Exposed electrode length: | 2.5 cm |
| Distance between electrodes: | 2.5 cm |
| Power setting: | 8 W |
| Ablation time: | 10 min. |
| Lesion size: | |
| width: | 2.8 cm |
| length: | 2.7 cm |
| depth: | 3.0 cm |

EXAMPLE 5

| | |
|---|---|
| Exposed electrode length: | 2.5 cm |
| Distance between electrodes: | 2.5 cm |
| Power setting: | 8 W |
| Ablation time: | 12 min. |
| Lesion size: | |
| width: | 2.8 cm |
| length: | 2.8 cm |
| depth: | 2.5 cm |

EXAMPLE 6

| | |
|---|---|
| Exposed electrode length: | 2.5 cm |
| Distance between electrodes: | 1.5 cm |
| Power setting: | 8 W |
| Ablation time: | 14 min. |
| Lesion size: | |
| width: | 3.0 cm |
| length: | 3.0 cm |
| depth: | 2.0 cm |

EXAMPLE 7

With return electrode at 1.5 cm

| | |
|---|---|
| Exposed electrode length: | 2.5 cm |
| Distance between electrodes: | 2.5 cm |
| Power setting: | 8 W |
| Ablation time: | 10 min. |
| Lesion size: | |
| width: | 3.0 cm |
| length: | 3.0 cm |
| depth: | 3.0 cm |

EXAMPLE 8

| | |
|---|---|
| Exposed electrode length: | 2.5 cm |
| Distance between electrodes: | 2.5 cm |
| Power setting: | 10 W |
| Ablation time: | 12 min. |
| Lesion size: | |
| width: | 3.5 cm |
| length: | 3.0 cm |
| depth: | 2.3 cm |

EXAMPLE 9

| | |
|---|---|
| Exposed electrode length: | 2.5 cm |
| Distance between electrodes: | 2.5 cm |
| Power setting: | 11 W |
| Ablation time: | 11 min. |
| Lesion size: | |
| width: | 3.5 cm |
| length: | 3.5 cm |
| depth: | 2.5 cm |

EXAMPLE 10

| | |
|---|---|
| Exposed electrode length: | 3.0 cm |
| Distance between electrodes: | 3.0 cm |
| Power setting: | 11 W |
| Ablation time: | 15 min. |
| Lesion size: | |
| width: | 4.3 cm |
| length: | 3.0 cm |
| depth: | 2.2 cm |

EXAMPLE 11

| | |
|---|---|
| Exposed electrode length: | 3.0 cm |
| Distance between electrodes: | 2.5 cm |
| Power setting: | 11 W |
| Ablation time: | 11 min. |
| Lesion size: | |
| width: | 4.0 cm |
| length: | 3.0 cm |
| depth: | 2.2 cm |

EXAMPLE 12

| | |
|---|---|
| Exposed electrode length: | 4.0 cm |
| Distance between electrodes: | 2.5 cm |
| Power setting: | 11 W |
| Ablation time: | 16 min. |
| Lesion size: | |
| width: | 3.5 cm |
| length: | 4.0 cm |
| depth: | 2.8 cm |

EXAMPLE 13

Two pairs of electrodes (Four electrodes)

| | |
|---|---|
| Exposed electrode length: | 2.5 cm |
| Distance between electrodes: | 2.5 cm |
| Power setting: | 12 W |

-continued

| | |
|---|---|
| Ablation time: | 16 min. |
| Lesion size: | |
| width: | 3.5 cm |
| length: | 3.0 cm |
| depth: | 4.5 cm |

EXAMPLE 14

Two pairs of electrodes (Four electrodes)

| | |
|---|---|
| Exposed electrode length: | 2.5 cm |
| Distance between electrodes: | 2.5 cm |
| Power setting: | 15 W |
| Ablation time: | 14 min. |
| Lesion size: | |
| width: | 4.0 cm |
| length: | 3.0 cm |
| depth: | 5.0 cm |

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An RF treatment system, comprising:

a first catheter including a first catheter lumen and a first catheter distal end;

a first needle electrode including a first needle electrode lumen and a first needle electrode distal end, the first needle electrode being at least partially positioned in the first catheter lumen;

a first insulator sleeve positioned in a slideable surrounding relationship to the first needle electrode to define a first needle ablation surface;

a second catheter including a second catheter lumen and a second catheter distal end;

a second needle electrode including a second needle electrode lumen and a second needle electrode distal end, the second needle electrode being at least partially positioned in the second catheter lumen;

a second insulator sleeve positioned in a slideable surrounding relationship to the second electrode to define a second needle ablation surface;

an RF power source connected to the first and second needle electrodes, the first and second needle electrodes providing bipolar RF ablation between the two needles in an ablation volume;

a deflectable introducer with a laterally deflectable distal end and an ablation volume temperature sensor positioned at the deflectable introducer distal end, the deflectable introducer distal end being advanced in and out of one of the distal end of the first or second needle electrodes to measure a temperature of tissue in the ablation volume; and an apparatus connected to the introducer for advancing the introducer in and out of one of the distal end of the first or second needle electrodes.

2. The RF ablation system of claim 1, further comprising:

a removeable first introducer positioned in the lumen of the first needle electrode including a first introducer distal end and a first introducer sensor positioned on a surface of the first introducer; and a removeable second introducer positioned in the lumen of the second needle electrode including a second introducer distal end and a second introducer sensor positioned on a surface of the second introducer.

3. The RF treatment system of claim 2, further comprising:

a return electrode coupled to the RF power source.

4. The RF treatment system of claim 3, further comprising:

a first insulator sleeve sensor positioned on a surface of the first insulator sleeve; and a second insulator sleeve sensor positioned on a surface of the second insulator sleeve.

5. The RF treatment system of claim 4, further comprising:

resources connected with the first introducer sensor, the second introducer sensor, the first insulator sleeve sensor, the second insulator sleeve sensor, the return electrode and the RF power source to maintain a selected power at the first and second needle electrodes independent of changes in current of voltage.

6. The RF treatment system of claim 3, further comprising:

resources connected with the first introducer sensor, the second introducer sensor, the return electrode and the RF power source to maintain a selected power at the first and second needle electrodes independent of changes in current or voltage.

7. The RF treatment system of claim 1, further comprising:

a first infusion device with a first infusion device lumen and distal end, the first catheter being partially disposed in the first infusion device and removeable therefrom.

8. The RF treatment system of claim 7, further comprising:

a second infusion device with a second infusion device lumen and distal end, the second catheter being partially disposed in the second infusion device and removeable therefrom.

9. The RF treatment system of claim 1, wherein the first and second needle electrode distal ends are sharpened.

10. The RF treatment system of claim 1, wherein the first and second needle electrodes are hollow and include fluid distribution ports.

11. An RF treatment system, comprising:

a first catheter including a first catheter lumen and a first catheter distal end;

a first needle electrode including a first needle electrode lumen and a first needle electrode distal end, the first needle electrode being at least partially positioned in the first catheter lumen;

a first insulator sleeve positioned in a slideable surrounding relationship to the first needle electrode to define a first needle ablation surface;

a second catheter including a second catheter lumen and a second catheter distal end;

a second needle electrode including a second needle electrode lumen and a second needle electrode distal end, the second needle electrode being at least partially positioned in the second catheter lumen;

a second insulator sleeve positioned in a slideable surrounding relationship to the second electrode to define a second needle ablation surface;

an RF power source coupled to the first and second needle electrodes and a return electrode, the first and second needle electrodes providing bipolar RF ablation between the two needles in an ablation volume;

a first needle electrode extension with a laterally deflectable distal end, the first needle electrode extension being positioned at the distal end of the first needle electrode, the first needle electrode extension being coupled to the RF power source and advanced in and out of the distal end of the first needle electrode to provide monopolar ablation; and an apparatus connected to the first needle electrode for advancing the first needle electrode extension in and out of the distal end of the first needle electrode.

12. The RF treatment system of claim 11, further comprising:

a second needle electrode extension with a laterally deflectable distal end, the second needle electrode extension being positioned at the distal end of the second needle electrode, the second needle electrode extension being coupled to the RF power source and advanced in and out of the distal end of the second needle electrode to provide monopolar ablation, wherein the apparatus for advancing the first needle electrode extension in and out of the distal end of the first needle electrode also advances the second needle electrode in and out of the second needle electrode.

13. The RF treatment system of claim 12, wherein the second needle electrode extension is made of a memory metal.

14. The RF treatment system of claim 13, wherein the second needle electrode extension is made of nitinol.

15. The RF treatment system of claim 12, wherein the second needle electrode extension includes a thermal sensor positioned at its distal end.

16. The RF treatment system of claim 12, further comprising:

a return electrode coupled to the RF power source and the first and second needle electrodes.

17. The RF treatment system of claim 16, further comprising:

resources connected with the first introducer sensor, the second introducer sensor, the first insulator sleeve sensor, the second insulator sleeve sensor, the return electrode and the RF power source to maintain a selected power at the first and second needle electrodes independent of changes in current of voltage.

18. The RF treatment system of claim 17, further comprising:

a second infusion device with a second infusion device lumen and distal end, the second catheter being partially disposed in the second infusion device and removeable therefrom.

19. The RF ablation system of claim 11, further comprising:

a removeable first introducer positioned in the lumen of the first needle electrode including a first introducer distal end and a first introducer sensor positioned on a surface of the first introducer; and a removeable second introducer positioned in the lumen of the second needle electrode including a second introducer distal end and a second introducer sensor positioned on a surface of the second introducer.

20. The RF treatment system of claim 19, further comprising:

a first insulator sleeve sensor positioned on a surface of the first insulator sleeve; and a second insulator sleeve sensor positioned on a surface of the second insulator sleeve.

21. The RF treatment system of claim 19, further comprising:

resources connected with the first introducer sensor, the second introducer sensor, the return electrode and the RF power source to maintain a selected power at the first and second needle electrodes independent of changes in current or voltage.

22. The RF treatment system of claim 11, further comprising:

a first infusion device with a first infusion device lumen and distal end, the first catheter being partially disposed in the first infusion device and removeable therefrom.

23. The RF treatment system of claim 11, wherein the first and second needle electrode distal ends are sharpened.

24. The RF treatment system of claim 11, wherein the first needle electrode extension is made of a memory metal.

25. The RF treatment system of claim 24, wherein the first needle electrode extension is made of nitinol.

26. The RF treatment system of claim 11, wherein the first needle electrode extension includes a thermal sensor positioned at its distal end.

27. An RF treatment system, comprising:

a first catheter including a first catheter lumen and a first catheter distal end;

a first needle electrode including a first needle electrode lumen and a first needle electrode distal end, the first needle electrode being at least partially positioned in the first catheter lumen;

a first insulator sleeve positioned in a slideable surrounding relationship to the first needle electrode to define a first needle ablation surface;

a second catheter including a second catheter lumen and a second catheter distal end;

a second needle electrode including a second needle electrode lumen and a second needle electrode distal end, the second needle electrode being at least partially positioned in the second catheter lumen;

a second insulator sleeve positioned in a slideable surrounding relationship to the second electrode to define a second needle ablation surface;

an RF power source coupled to the first and second needle electrodes, the first and second needle electrodes providing bipolar RF ablation between the two needles in an ablation volume;

a first needle electrode extension with a laterally deflectable distal end, the first needle electrode extension being positioned at the distal end of the first needle electrode, the first needle electrode extension being coupled to the RF power source and advanced out of the distal end of the first needle electrode to provide monopolar ablation;

a deflectable introducer with a laterally deflectable distal end and an ablation volume temperature sensor positioned at the deflectable introducer distal end, the deflectable introducer distal end being advanced out of one of the distal end of the first or second needle electrodes to measure a temperature of tissue in the ablation volume; and an apparatus connected to the introducer for advancing the deflectable introducer distal end out of one of the distal end of the first or second needle electrodes.

* * * * *